(12) United States Patent
Israelowitz et al.

(10) Patent No.: US 9,057,044 B2
(45) Date of Patent: Jun. 16, 2015

(54) LAMINAR FLOW REACTOR

(76) Inventors: Meir Israelowitz, Toronto (CA);
Herbert Peter von Schroeder, Toronto (CA); Syed Rizvi, Lake Mary, FL (US); Chris Holm, Wuppertal (DE); Christoph Gille, Hohen Herrendorf (DE)

(*) Notice: Subject to any disclaimer, the term of this patent is extended or adjusted under 35 U.S.C. 154(b) by 380 days.

(21) Appl. No.: 13/359,689

(22) Filed: Jan. 27, 2012

(65) Prior Publication Data

US 2012/0164623 A1    Jun. 28, 2012

Related U.S. Application Data

(63) Continuation-in-part of application No. 11/895,645, filed on Aug. 27, 2007, now abandoned.

(60) Provisional application No. 60/838,494, filed on Aug. 30, 2006.

(51) Int. Cl.
*C12M 3/00* (2006.01)
*C12M 1/00* (2006.01)
*C12M 1/12* (2006.01)
*C12M 1/34* (2006.01)

(52) U.S. Cl.
CPC .............. *C12M 21/08* (2013.01); *C12M 23/00* (2013.01); *C12M 25/14* (2013.01); *C12M 41/00* (2013.01)

(58) Field of Classification Search
CPC ...... C12M 21/08; C12M 23/00; C12M 25/14; C12M 41/00
USPC ........................................... 435/283.1–309.4
See application file for complete search history.

(56) References Cited

U.S. PATENT DOCUMENTS

| 4,032,407 A | 6/1977 | Scott et al. |
|---|---|---|
| 4,095,974 A | 6/1978 | Matovich |
| 4,636,473 A | 1/1987 | Kleinstreuer |
| 4,649,117 A | 3/1987 | Familletti |
| 4,654,308 A | 3/1987 | Safi |
| 4,833,081 A | 5/1989 | Walker |
| 4,833,083 A | 5/1989 | Saxena |
| 4,833,089 A | 5/1989 | Kojima et al. |
| 4,889,812 A | 12/1989 | Guinn et al. |
| 4,892,818 A | 1/1990 | Ramp |
| 4,894,342 A | 1/1990 | Guinn et al. |
| 4,931,401 A | 6/1990 | Safi |
| 4,937,196 A | 6/1990 | Wrasidlo et al. |
| 5,057,428 A | 10/1991 | Mizutani |

(Continued)

OTHER PUBLICATIONS

A History of Suction-Type Laminar-Flow Control with Emphasis on Flight Research, Monograph in Aerospace History 13, NASA, 1999 at p. 2.

*Primary Examiner* — Nathan Bowers
*Assistant Examiner* — Lydia Edwards
(74) *Attorney, Agent, or Firm* — Peter A Haas Esquire LLC

(57) ABSTRACT

The present invention describes a laminar flow bioreactor with improved laminar flow lines of fluids. The bioreactor housing defines a chamber adapted to receive a scaffold. An inlet aperture at one end of the chamber is in fluid communication with an outlet aperture at the opposite end of the chamber. A bypass mechanism selectively operable from an open position to a closed position consisting of an iris assembly directs a portion of fluid flowing through the chamber around the scaffold-receiving area. This bioreactor is inserted in a bioreactor system.

5 Claims, 16 Drawing Sheets

(56) References Cited

U.S. PATENT DOCUMENTS

| | | | |
|---|---|---|---|
| 5,081,035 A | * | 1/1992 | Halberstadt et al. ....... 435/297.4 |
| 5,137,828 A | | 8/1992 | Robison |
| 5,155,035 A | | 10/1992 | Schwarz |
| 5,155,219 A | | 10/1992 | Kim et al. |
| 5,158,593 A | | 10/1992 | Delima |
| 5,256,570 A | | 10/1993 | Clyde |
| 5,308,764 A | | 5/1994 | Goodwin |
| 5,320,963 A | | 6/1994 | Knaack et al. |
| 5,376,548 A | | 12/1994 | Matsuo et al. |
| 5,476,783 A | | 12/1995 | Matsakis et al. |
| 5,494,574 A | | 2/1996 | Unterman |
| 5,494,577 A | | 2/1996 | Rekers |
| D370,263 S | | 5/1996 | Falkenberg et al. |
| 5,527,467 A | | 6/1996 | Ofsthun |
| 5,531,897 A | | 7/1996 | Stormo |
| 5,556,765 A | | 9/1996 | Dedolph |
| 5,563,068 A | | 10/1996 | Zhang |
| 5,565,361 A | | 10/1996 | Musakis et al. |
| 5,587,298 A | | 12/1996 | Horigane |
| 5,605,835 A | | 2/1997 | Hu et al. |
| 5,622,819 A | | 4/1997 | Herman |
| 5,705,390 A | | 1/1998 | Kadouri et al. |
| 5,763,267 A | | 6/1998 | Kurian et al. |
| 5,846,816 A | | 12/1998 | Forth |
| 5,882,918 A | | 3/1999 | Goffe |
| 5,955,353 A | | 9/1999 | Amiot |
| 5,998,184 A | | 12/1999 | Shi |
| 6,001,642 A | | 12/1999 | Tsao |
| 6,133,019 A | | 10/2000 | Herman |
| 6,159,739 A | | 12/2000 | Weigle et al. |
| 6,168,949 B1 | | 1/2001 | Rubenberger |
| 6,214,617 B1 | | 4/2001 | Herman |
| 6,217,937 B1 | | 4/2001 | Shealy |
| 6,228,607 B1 | | 5/2001 | Kersten |
| 6,423,229 B1 | | 7/2002 | Mao |
| 6,566,126 B2 | | 5/2003 | Cadwell |
| 6,582,596 B2 | | 6/2003 | Mao |
| 6,582,955 B2 | | 6/2003 | Martinez et al. |
| 6,589,780 B2 | | 7/2003 | Banerjee et al. |
| 6,632,657 B1 | | 10/2003 | Kislyh |
| 6,632,658 B1 | | 10/2003 | Schob |
| 6,670,169 B1 | | 12/2003 | Schob |
| 6,670,173 B1 | | 12/2003 | Schels et al. |
| 6,680,166 B1 | | 1/2004 | Mullon et al. |
| 6,752,921 B1 | | 6/2004 | Kulick |
| 6,844,187 B1 | | 1/2005 | Wechler et al. |
| 6,867,040 B2 | | 3/2005 | Helmstetter et al. |
| 6,933,144 B2 | | 8/2005 | Cadwell |
| 2001/0006043 A1 | | 7/2001 | Shealey et al. |
| 2004/0248167 A1 | | 12/2004 | Quake et al. |
| 2004/0266022 A1 | | 12/2004 | Sundararajan et al. |
| 2007/0036678 A1 | | 2/2007 | Sundararajan et al. |
| 2007/0111310 A1 | * | 5/2007 | Cohen et al. ................. 435/366 |

\* cited by examiner

FIG. 8
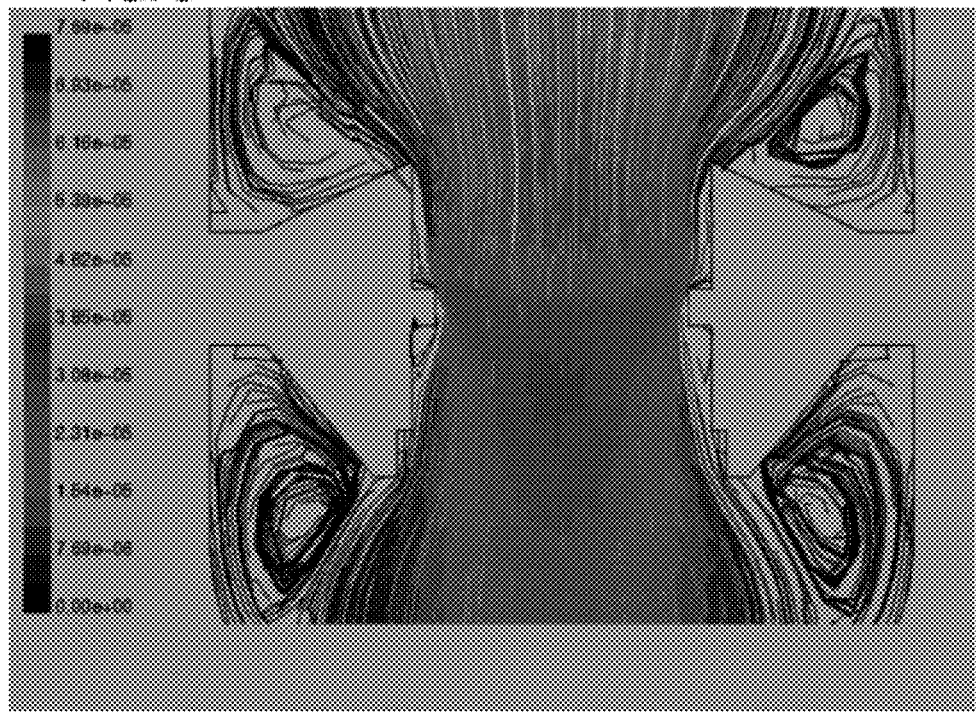
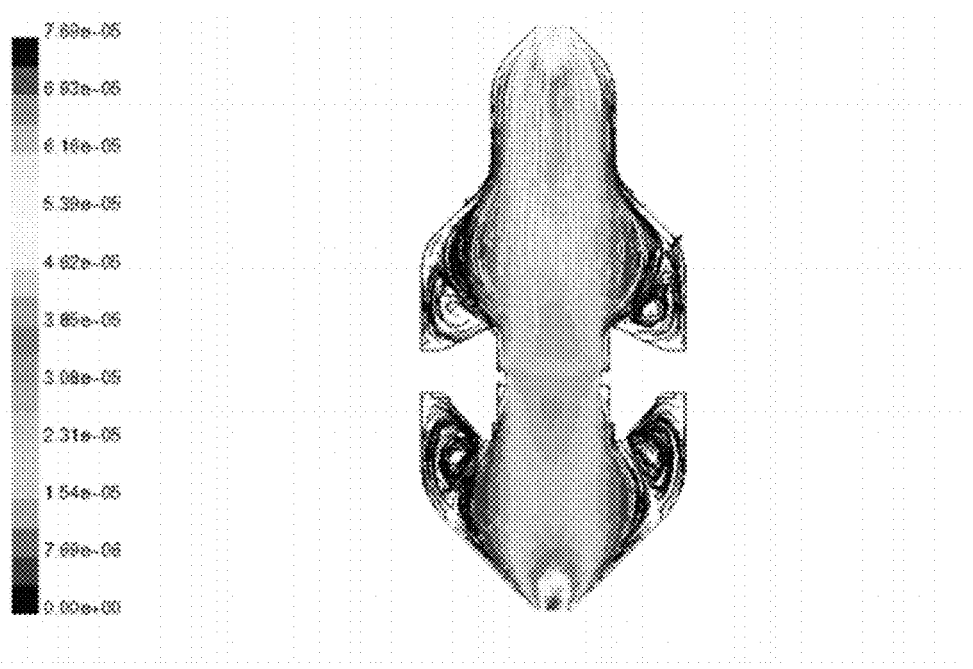

Table 1. Scaffold parameters for CFD simulation

| Permeability, $\kappa$, $m^2$ | Porosity, $\varepsilon$ | Viscous resistance coefficient, $1/\kappa$, $1/m^2$ | Inertial resistance coefficient, $C_2$, $1/m$ | Particle diameter, $D_p$, m |
|---|---|---|---|---|
| $4.5200 \times 10^{-12}$ | $8.0000 \times 10^{-1}$ | $2.2124 \times 10^{12}$ | $5.9404 \times 10^{5}$ | $2.3015 \times 10^{-6}$ |
| $5.0000 \times 10^{-12}$ | $8.0000 \times 10^{-1}$ | $2.0000 \times 10^{11}$ | $1.7861 \times 10^{5}$ | $7.6547 \times 10^{-6}$ |
| $5.0000 \times 10^{-11}$ | $8.0000 \times 10^{-1}$ | $2.0000 \times 10^{10}$ | $5.6481 \times 10^{4}$ | $2.4206 \times 10^{-5}$ |
| $5.0000 \times 10^{-10}$ | $8.0000 \times 10^{-1}$ | $2.0000 \times 10^{9}$ | $1.7861 \times 10^{4}$ | $7.6547 \times 10^{-5}$ |
| $5.0000 \times 10^{-9}$ | $8.0000 \times 10^{-1}$ | $2.0000 \times 10^{8}$ | $5.6481 \times 10^{3}$ | $2.4206 \times 10^{-4}$ |

FIG. 16

Table 2. Comparison of CFD simulation results for pressure variation across the scaffold in different designs of bioreactor

|  | Design 1 | Design 2 | Design 3 | |
|---|---|---|---|---|
|  |  |  | Irises closed | Irises open |
| Upstream Pressure [Pa] | $6.04 \times 10^{-3}$ | $8.32 \times 10^{-3}$ | $4.93 \times 10^{-3}$ | $1.08 \times 10^{-2}$ |
| Downstream Pressure [Pa] | 0 | 0 | 0 | $8.97 \times 10^{-3}$ |

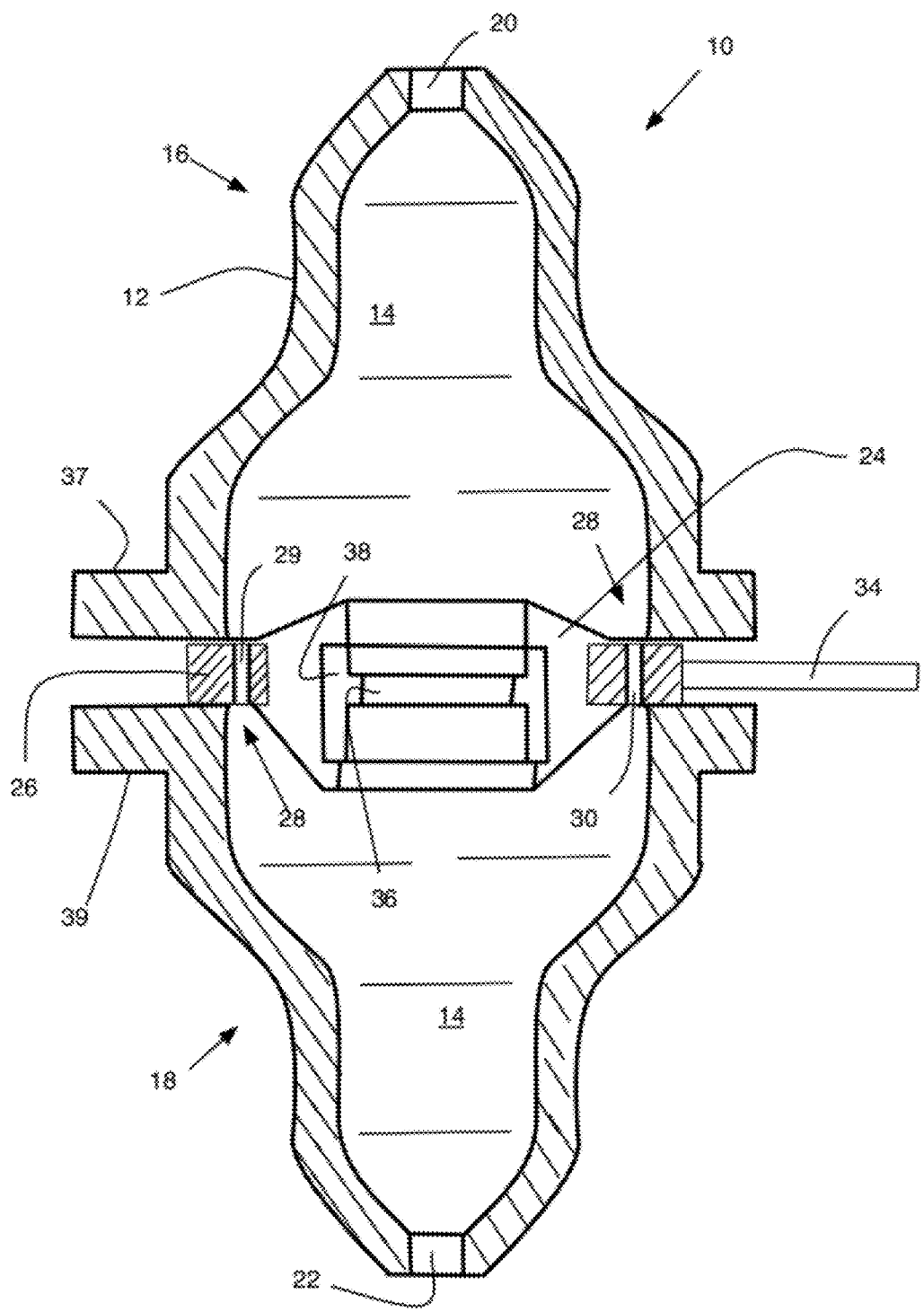

LAMINAR FLOW REACTOR

PRIORITY CLAIM

The present application is a continuation in part and, therefore, claims benefit under 35 USC Section 120 of U.S. Non-Provisional patent application Ser. No. 11/895,645 filed on Aug. 27, 2007. The non-provisional application, in turn, claims benefit under 35 USC Section 119(e) of U.S. Provisional Patent Application Ser. No. 60/838,494 filed on August 2006. The present application is based on and claims priority from these applications, the disclosures are hereby expressly incorporated herein by reference. Further, the present invention includes all the same common inventors from the parent application.

BACKGROUND AND FIELD OF THE INVENTION

The reactor of the invention relates to explore the characteristics of biological materials and allows for the culture and growth of such materials. These characteristics are important for tissue engineering applications, which include but are not limited to replacement of tissues such as skin and bone or replacement of organs or parts thereof. Existing bioreactors or fermentors have the capacity for growing small quantities of tissue. A limitation of fermentor devices of the prior art include an inherent design issue that allows for, or in some cases, creates shear forces, which contributes to a high mortality of the cells being cultured. Many existing bioreactors require enzyme kinetics, membrane exchange, or use rotational designs to mimic a micro-gravity environment, and as such, these prior-art devices have undesirable limitations, as will be discussed below.

By definition, a reactor is described as a mass-transfer of rate controls and of rate of reaction. The intrinsic catalyzed reaction rate must establish the rate expression. The design must either incorporate both the reaction rate and the mass-transfer rate or neglect the reaction rate with justification by comparison with the mass-transfer rate.

Reactor designs are categorized for industrial and small scale. The following bioreactors models bioreactors are being used today: Rotational reactors use continuous spin to mimic a microgravity environment. The spin reduces the hydrodynamic shear ten-fold. The reduction of shear is important to maintain the cell structure and integrity. Another property in the design is the increased mass transfer to support large aggregates. A limitation with this design is that it cannot be used to adequately control the growth of large amounts of cells in a scaffold.

Stirred methods, or suspension bioreactors are commonly used in life sciences and chemical research. The major limitation of these types of bioreactors is that the design cannot be transferred to industrial sizes. By scaling-up such bioreactors, the resulting increase in the shear forces limits the sizes of cultures and hence limits the practical applications.

Industrial scale bioreactors include, for example, the Air Lift Bioreactor. The Air Lift reactor is a low energy input, high yield alternative to stirred tank bioreactors. Its low shear action allows for good oxygen transfer, but the tissue culture sizes and volumes cannot be adequately controlled.

The terms reactors or fermentors are commonly used in the trade because they describe a control mass-transfer and a control rate of reaction in the mass-transfer.

Typical bioreactors or fermentors of this type are shown, for example, in the many United States of America patents, a list of which is included in an information disclosure statement sheet, which is considered a part of this specification and all the publications and patents mention therein, are hereby incorporated by reference in their entirely as if each individual publication or patent was specifically and individually indicated to be incorporated by reference. In case of conflict, the present application, including any definition herein, will control.

It is well known in the art that the growth and production of biological mater requires medium for cell and tissue nourishment. Exchange of medium is vital to supply such nourishment as well as remove toxins, metabolic end products, and waste. The exchange and flow of medium is optimally achieved by a laminar flow over and around the cells and through supportive scaffolding. The laminar flow reduces turbulence and shear forces that otherwise impede the growth of the biological material. Laminar flow can also allow for the rapid exchange of nutrients and waste products.

Therefore there is a need for a non-rotating bioreactor capable of growing large volumes or amounts of tissue by controlling the shear forces.

SUMMARY OF THE INVENTION

The present invention overcomes many of the limitations of known devices in the prior art. Specifically, the present invention incorporates elements that reduce shear forces in the artificial growth of biological matter, such as cells. The hydrodynamic shear forces are reduced by the shape of the bioreactor and by maintaining laminar flow of the medium. Laminar flow is achieved by a (typically peristaltic) pump and pressure sensors that control and steer the flow of medium. Further, such an improved non-rotating reactor should include a design that allows for the placement of a scaffold in the middle of the device. The purpose of the scaffold is to support cell growth and provide structural integrity of the tissue or organ. The cells can proliferate and differentiate within or on the scaffold. Providing optimal delivery of a medium and accounting for optimal shear forces is vital to reduce cell death and to increase the rate of adaptation for the cells in the scaffold.

The present invention introduces a large-scale bioreactor that greatly reduces shear stresses on a large-scale cell culture. The present invention is termed a "Laminar Flow Reactor", which enables a three-dimensional volume of cells to be generated artificially. The Laminar Flow reactor consists of an upper housing and a lower housing. The housings are interconnected by a plurality of connectors and a plurality of rigid spacers, an inlet fluid, an outlet fluid, a fluid reservoir, and a means for transporting fluid within the system. During treatment, liquid media is transported from the fluid reservoir to the inlet manifold, which will in turn evenly distribute the media to each of the connected connectors and internal culture pockets. Laminar flow through the device is maintained by the cylindrical shape of the device and by a bypasses mechanism. An outlet fluid manifold is also provided to ensure that each treatment chamber is evenly filled and to ensure that any air bubbles formed during treatment are removed from the treatment chambers.

The present invention brings additional components to optimize laminar flow of fluid and thereby stimulate cell growth in three dimensions. Fluid flow is achieved through the cellular biological sample and through a bypass mechanism with variables openings. By optimizing laminar flow, turbulence is reduced. For this purpose the reactor consists of a housing that includes a chamber for intake of biomaterial and variable bypasses around the chamber.

The flow through this reactor vessel can be precisely controlled without influencing or controlling the pump, thus improving pump efficiency. Specials features of this bioreactor are the two rings around the chamber that have openings for directing the fluid flow through a bypass as needed to control the flow.

In a preferred embodiment, the reactor vessel of the present invention includes a handle on anyone of the rings with an iris to open and close the openings to steer the flow. The iris can operate manually or by a motor and could be automated in operation according to various operational parameters. In such an embodiment, the reactor can contain pressure sensors to control the handle and iris and hence the fluid flow.

It is an advantage to have a window at the output of the chamber showing the kind of flow. The device can also verify or quantify the flow. An advantage of the laminar flow bioreactor is the whole biomaterial will have access to medium and a result is the cells will growth in a 3-Dimensional growth.

A second advantage is that the flow produced and creates a microgravity environment, which helps in the initial cell development.

A third advantage is by having laminar flow the shear force will not destroy the cells.

Various preferred embodiments of the present invention include a Laminar flow reactor for three dimensional cell growth comprising, in part or in combination any of the following: a housing including a chamber for intake of bio-material and variable bypasses around the chamber; a combination of two houses and assembly of bypasses; a plurality interlock bypasses and the bypasses are connected to the upper house; a plurality of interlock bypasses and the bypasses are connected to the lower house; a combination of plurality of bypasses as an integral part of the upper house; a combination of plurality of bypasses as an integral part of the lower house; a reactor according claim 1 is a combination of plurality of bypasses and an integral part of either the upper house or the lower house or both the houses; having two rings around the chamber having openings for steering the flow through the bypass; having two rings around the chamber in combination with a of plurality of bypasses connected to the upper house; having two rings around the chamber in combination with a plurality of bypasses connected to the lower house; having two rings around the chamber in combination with a plurality of bypasses integral of the upper house; having two rings around the chamber in combination of a plurality of bypasses integral to either or both of the upper and lower houses; a reactor with a handle on a ring with iris to open and close the openings to steering the flow; a reactor with a handle on a ring with iris to open and close the openings to steer the flow and a plurality of bypasses connected to the upper house; a reactor with a handle on a ring with iris to open and close the openings to steer the flow and a plurality of bypasses connected to the lower house; a reactor with a handle on a ring with iris to open and close the openings to steer the flow and a plurality of bypasses connected to the houses; a reactor with a handle on a ring with iris to open and close the openings to steer the flow combination of a plurality of bypasses integral of the upper house; a reactor with a handle on a ring with iris to open and close the openings to steer the flow combination of a plurality of bypasses integral of the lower house; a reactor with a handle on a ring with iris to open and close the openings to steer the flow combination of a plurality of bypasses integral of the houses; a reactor with sensors steering the motion of a motor moving the handle; a reactor according with sensors steering the motion of a motor moving the handle and a plurality of bypasses connected to the lower or upper house; a reactor with sensors steering the motion of a motor moving the handle and a plurality of bypasses connected to the lower house; a reactor with sensors steering the motion of a motor moving the handle and a plurality of bypasses connected to the either or both houses; a reactor with sensors steering the motion of a motor moving the handle and combination of a plurality of bypasses integral of the upper house; a reactor with sensors steering the motion of a motor moving the handle in combination with a plurality of bypasses integral of the lower house; a reactor with sensors steering the motion of a motor moving the handle combination of a plurality of bypasses integral to either or both of the houses; a reactor with a chamber with a grid to support the bio-material; a reactor with a chamber with a grid to support the bio-material and a plurality of bypasses connected to the upper house or connected to the lower house, or connected to either or both houses; a reactor with a chamber with a grid to support the bio-material combination of a plurality of bypasses integral to the upper house, integral to the lower house, integral to either of the houses, or integral to both of the houses; a reactor with a window at the output of the chamber showing the kind of flow and the plurality of bypasses connected to the house; a reactor according to claim 1 with a window at the output of the chamber showing the kind of flow; a reactor with a window at the output of the chamber showing the kind of flow and the plurality of bypasses connected to the upper house, or connected to the lower house, or bypasses integral to the upper house or integral to the lower house or connected to or integral to either or both of the houses.

The present invention, a bioreactor, includes the assembly and all the connected parts. The upper house couples or is connected with a top flange. The scaffold holder is in the middle, with the grid. The iris handle (bypass mechanism) is connected with the iris clamp and the lockring. The lower flange is connected with or couples to the lower house.

The reactor vessel is configured by having an upper house coupled to the lower house. The upper house and the lower house are the primary contributors to the inside shape of the bioreactor and the shape is important for the laminar flow. The top flange is a single piece part (it is coupled to or is formed as part of or is integral to) the upper house. The lower flange is a single piece part of the lower house. The SS rings: these two rings provide the sealing surface for both the top and bottom half of the assembly as well as either side of iris handle. A total of four o-rings interact with the two rings. The SS-rings not only provide for the overflow system but also serve as the primary structural components that hold the iris clamp assembly as well as the scaffold holder and the scaffold itself. The flat area on the inside diameter of the part interfaces with the notch out of the protrusion of iris clamp to ensure that the corresponding SS-rings are correctly positioned relative to each other. When assembled, both SS-rings line up with each other. When the iris handle is rotated, one should be able to see through the overflow valves (all three layers). The iris handle is the only moving part in the assembly, which allows the size of the overflow valves to be modified. To maintain the sealing provide by the two grooves, one on each side, two o-rings were seated (not showing in this drawing). Between the SS-ring and the scaffold holder they are two grooves with the second set O-rings for sealing internal leakages.

The arm extending from the circular portion of the part functions to connect to the computer and controlled linear actuator to change the valving incrementally as conditions across the scaffold (bio-material) change. The iris clamp provides support for the scaffold basket as well as a surface and mass to clamp the whole valve/scaffold support subassembly together.

The outer section of the iris clamp provides the contact surface for the bottom of the SS ring iris handle assembly (the top is provided by lockring and the inner is a resting point for the scaffold holder. The flat is simply to keep the valving subassembly properly aligned. The lockring is simply the part that allows the valving subassembly to be held firmly together. To complete this assembly, screws are put through lockring and well into iris clamp. The shape of lockring is nothing more than an attempt at making the fluid flow within the bioreactor more suitable. This shape can be modified to better suit the application.

The scaffold holder fits in the assembly is designed to be interchangeable. The scaffold holder is a cylinder with a tab around the circumference of the inside and a groove around the outside circumference. A number of small holes are drilled parallel to each other across the center of this groove and along the rim around the inside give the support for the scaffold.

The upper house is in place with the top flange. The scaffold holder is located in the middle of the assembly. Two SS-rings hold the iris holder (iris clamp). Two set's of O-rings seal internal leaks in the houses. The iris holder is connected to the control box, moving the handle opens or closes the bypasses. The iris clamp holds the irises in place. The lower house in the end of the assembly is with the lower flange.

One advantage of the present invention includes the ability to grow a biomaterial seeded with cells. In a certain time frame, the cell-seeded biomaterial is proliferated in a bioreactor or a fermenton. Once the biomaterial is populated with cells it usually is removed from the bioreactor or fermenton. To achieve longer time of proliferation, and thereby increase the mass of cells growing on the bioreactor or fermenton, the bioreactor or fermenton must provide a means to overcome shear stresses or turbulence due to stagnation of the flow on the biomaterial.

Without this means, the stagnation shear stresses rip apart the cells and create an unacceptably high mortality rate or apoptosis. To overcome this weakness the present innovation utilizes laminar flow equations. In particular, the differential pressure that causes this shear stresses and turbulence is bypassed by a bypass relieve device.

In the present invention, we control, flow and turbulences via the differential pressure, where the top pressure from the inlet and the low pressure of the outlet is release via a bypass device so flow can go through or around the biomaterial, as needed.

The well-studied Laminar Flow was introduced in 1888 by Osborne Reynolds, who shows visually the transition from Laminar Flow to Turbulent flow, termed Reynolds number.

$$\text{Reynolds Number} = Vd/u, \quad \text{Equation 1,}$$

where V is the average flow velocity, d is the diameter of the chamber and u is Kinematic Velocity.

$$\text{And Laminar Flow} = DP/2Lm(R2-r2), \quad \text{Equation 2.}$$

Where DP is the pressure, m is the viscosity of the fluid, L is the length of the pipe, R is the outer radius and r is inner radius of the flow. (see e.g., Braslow A, "A History of Suction-Type Laminar-Flow Control with Emphasis on Flight Research", *Monograph in Aerospace History* 13, NASA, 1999 at page 2).

DRAWING

FIG. 8 is a representational diagram showing laminar flow path lines of the third embodiment of the present invention.

FIG. 15 is a table defining scaffold parameters for CFD simulation according to one embodiment of the present invention.

FIG. 16 is a table comparing CFD simulation results for various bioreactors according to several embodiments of the present invention.

FIG. 17 is a cross-sectional front view of one preferred bioreactor according to one embodiment of the present invention.

DESCRIPTION OF THE INVENTION

Figure 1:
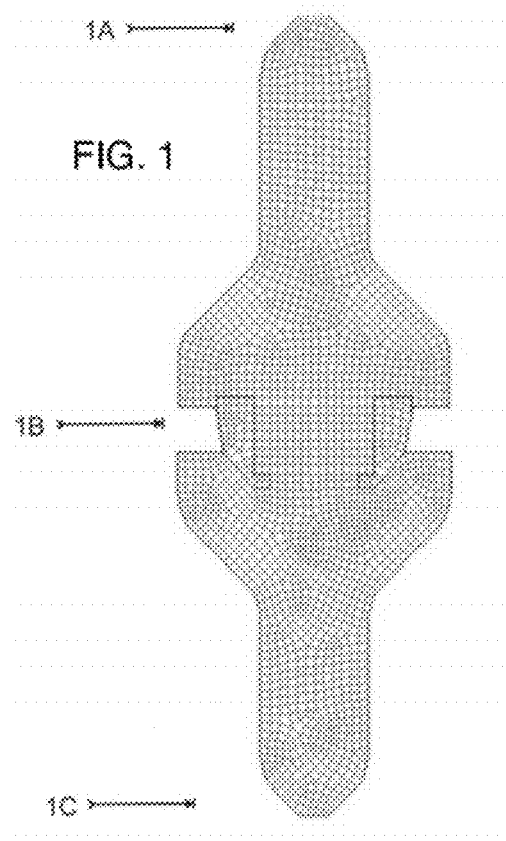
FIG. 1 is a representational front view of a first bioreactor design according to one embodiment of the present invention.

Possible preferred embodiments will now be described with reference to the drawings and those skilled in the art will understand that alternative configurations and combinations of components may be substituted without subtracting from the invention. In some figures of the drawing certain components may be omitted to more clearly illustrate aspects of the claimed invention.

To better understand the present invention over the state of the art, a representative bioreactor of the state of the art is disclosed by Cohen et al. in United States Published Application Number 2007/0111310, wherein a common problem of shear stresses of bioreactor material is addressed by controlling the flow rate across the scaffold.

Also known in this art, different perfusion bioreactors have been developed for tissue engineering applications, especially for bone tissue engineering. However, many systems were characterized only by perfusion rate and lack substantial information about shear stress within the reactor vessel. The results of our study suggest that reactor geometry has a significant impact on flow perfusion and pressure distribution around the scaffold. Common designs such as bell-shaped and cylindrical vessels cannot guarantee continuous perfusion across scaffolds without creating areas of flow stagnation or pressure build-up, as demonstrated in our CFD simulation results. Furthermore, our results show that increase in permeability of the scaffold due to cellular growth has an impact on flow vectors and pressure distribution.

The present invention, in contrast, recognizes that the shear stresses can be reduced by providing an alternate path of flow around the biomaterial in the reactor. Thus, a preferred embodiment of the present invention uses the novel approach of an internal bypass system in the form of a plurality of irises, which in testing successfully reduced upstream pressure build-up due to cellular growth within the scaffold. Furthermore, opening of the iris reduced the Reynolds number to change the flow pattern from turbulent to laminar flow. The iris system however requires a fine balance since its size can determine the amount of perfusion through the scaffold as well as the pressure drop across the scaffold. By balancing with the iris system, a laminar flow can be achieved within the bioreactor despite cellular growth in the scaffold.

In a preferred embodiment consists of a reactor housing consisting of a top cylinder housing and a bottom cylinder housing. Many materials, particularly biologically inert materials are well suited for these components and in one successful embodiment the top and bottom cylinder housings were machine lathed from a solid 2.5-inch block of polycarbonate rod.

The top cylinder housing and bottom cylinder housing define an interior volume that form the shape of the bioreactor in which the biomaterial will be grown. The shape of the interior volume is relatively important. Each housing half includes an opening at their distal end and in one contemplated embodiment the respective distal end opening of the top and bottom housings and this opening is about 0.25-inches in diameter and is adapted by means of drilling and tapping threads to receive a ⅛"NPT connector for the connection to the rest of the system. The major diameter (2.5") on the lip of each should be lessened be several thousandths when machined to be able to slide freely into the holes in the flanges. The same goes for the adjacent 2.375" diameter, which forms the outside of the major cylindrical component. All other dimensions should be machined as marked although the interior and exterior radii are noncritical.

After machining, these two parts should be fitted with four narrow dowels protruding from the flat edge parallel with the major axis. These interact with the tabs on a stainless steel ring to help align and seal the top cylinder housing to the bottom cylinder housing.

In a preferred embodiment the top and bottom cylinder housings are separate pieces to aid in manufacturing and to provide an opening to insert a screen for growing the biological material. Because these two halves need to releasably couple together, these housings include a flange, the top cylinder housing includes a top flange and the bottom cylinder housing includes a bottom flange and in one embodiment the flange material is a ⅜-inch polycarbonate sheet that is adhered to the respective housing body. Again, other bio-inert material would work equally well and only the fabrication method would change depending on the material selected for manufacturing.

In a preferred embodiment, these flanges should be glued as appropriate to the top cylinder housing at the proximal end having a large opening and to the bottom cylinder housing at its proximal end with the similarly sized large opening. The flanges cooperating with the cylinder housing halves thus form the top and bottom halves of the assembly. These were specified as separate parts to ease machining and to save on material. As these parts are mirror images of each other, when fitted with the rest of the assembly they should correspond with each other. The irregularities in the polygonal shape allow the arm on TEFLON_IRIS to protrude and also provide a mount point for an actuator if one is desired. The surface extending away from the cylindrical form should be sufficient to allow whatever means of clamping is decided on. As this has not yet been determined yet, the drawings do not reflect any such clamping device.

Sealing Rings, made from inert stainless steel or aluminum, the sealing rings align with the housing halves to create the sealed interior chamber of the bioreactor. In a preferred embodiment, the sealing rings consist of a 317 stainless steel sheet at 0.030 (alternatively a 3003 aluminum sheet at 0.063 used in prototype works equally well).

These two sealing rings provide the sealing surface for both the top and bottom half of the assembly as well as either side of the iris mechanism. A total of four o-rings interact with the two rings. 317 stainless was initially chosen for its reasonable strength and high corrosion resistance but machining the small grooves proved extremely difficult. When the material was switched to aluminum, the thickness was increased to provide enough stiffness for the assembly. These parts not only provide for the overflow system but also serve as the primary structural components that hold the iris clamp assembly as well as the scaffold holder and the scaffold itself.

The flat area on the inside diameter of the part interfaces with the notch out of the protrusion of iris clamp assembly to ensure that the both sealing rings are correctly positioned relative to each other.

When assembled, both sealing rings should line up with each other. When the iris mechanism is rotated, one should be able to see through the overflow valves (all three layers).

The iris mechanism consists of a ³⁄₁₆-inch PTFE sheet material that is machined on a CNC mill. This is the only moving part in the assembly, and it allows the size of the overflow (bypass mechanism) valves to be modified. Teflon was initially chosen to act as a seal between the two sealing ring parts while also reducing the friction involved in rotating the part. The factory finish was clearly not suitable to provide such a seal so two grooves, one on each side, were added to seat two o-rings. The depth of the grooves was eyeballed to hopefully contain the entirety of the o-ring when it is compressed so that there is as little separation between the iris mechanism and sealing rings as possible while still maintaining a good seal. The arm extending from the circular portion of the part was originally intended to connect to a computer controlled linear actuator capable of changing the valving incrementally as conditions across the scaffold change. Although there will be no actuator in this prototype, the arm should still provide plenty of stiffness to effectively change the state of the bioreactor.

The iris clamp assembly and related iris mechanism can be fabricated or machined from a polycarbonate rod or mass using various known machining methods including lathe, for example. The iris clamp assembly provides support for the scaffold basket as well as a surface and mass to clamp the whole valving/scaffold support subassembly together. The thickness of the walls of the basic cylinder shape should be sufficient to accept at least a #4 screw if not a #6. There is a lip on both the inner and outer surface of the bottom of the part. The outer provides the contact surface for the bottom of the iris assembly (the top is provided by a lockring) and the inner is a resting point for the scaffold holder. As explained above, the flat is simply to keep the valve subassembly properly aligned.

The lockring can be fabricated from a polycarbonate rod or other similar material. The lockring is simply the part which allows the valve subassembly to be held firmly together. To complete this assembly, Screws are put through lockring and well into the iris clamp assembly. The shape of the lockring is simply nothing more than an attempt at making the fluid flow within the bioreactor more suitable. This shape is certainly one that can be easily modified to better suit the application. The current one is most likely far too thin towards the edges and the sharp angle near the center should be rounded to help fluid flow.

Since it is possible that this bioreactor may at some point be used without enabling the overflow valves (in the case that a perforated scaffold is used) this lockring could easily be replaced with a part capable of both sealing off the overflow slots and also closing off the sides of the upper chamber, creating a nearly straight, cylindrical path from the top of the bioreactor to the scaffold.

The scaffold holder of one preferred embodiment of the present invention fits in the assembly and is designed to be as easily interchangeable as possible. The current version is a simple cylinder with a tab around the circumference of the inside and a groove around the outside circumference. A number of small holes are drilled parallel to each other across the center of this groove. In the final assembly, wire would be carefully woven back and forth at a 4 mm spacing. This along with the rim around the inside would produce plenty of support for the scaffold. After the growth cycle, the wire could be cut to remove the scaffold even if the tissue has grown around it. The machining could be done by cutting out one side, flipping it to cut the remainder of the cylinder, leaving the groove, and then mounting it in a vise and using the fourth axis of the mill to hold and rotate the part while the groove is cut.

Some of the contemplated o-rings in the present invention are $\frac{1}{16}$-inch silicone. Originally Teflon was selected for the o-rings but its lack of compressibility produced doubts as to whether it would be able to produce a good seal. Silicone has much greater compressibility but will also produce much more friction for the iris mechanism.

The present invention in its various embodiments was developed after both laboratory analysis using prototype reactors and computer simulations of reactor designs. To better understand the present invention, first an overview of known bioreactors and their inherent problems is needed. One such limitation known in the art is cell death. To prevent cell death, some prior-art bioreactors have been proposed based on rotational designs to mimic a micro-gravity environment including a membrane exchange unit for metabolites and gases. Such rotational models have been shown to reduce the hydrodynamic shear by approximately 10-fold. Lowering this hydrodynamic shear is important to maintain cell viability and tissue structure.

Another example of a rotational bioreactor that includes design properties to increase mass transfer and support large aggregates of cells is the laminar Taylor vortex that maintains oxygenation for long-term cell culture. However, a limitation with this design is that the tissue size cannot be adequately controlled and the growth of large amount of cells in the scaffold remains a challenge. Yet other bioreactor designs incorporated medium stirring or cell suspension methodologies such as microcarrier-based cultures.

But, the overall limitation of known bioreactors is how to reduce hydrodynamic shear stress caused by the scaffold in the reactor, and this stress causes cells to die. Experimental studies on suspension-adapted mammalian cells found turbulent shear more damaging to cells than laminar shear of the same magnitude. Results from studies of shear impact on adherent mammalian cells in 2D and 3D culture demonstrated multiple influences on cell proliferation, cell attachment and cell differentiation. Since responses differ among cell types and sources as well as variable culture and stress conditions, there is a need particularly for well-defined 3D culture systems for comparison of standardized cell culture.

Known bioreactor designs are different between industrial and laboratory small-scale applications. The latter designs are commonly for research purposes, but cannot be transferred to industrial scale for the growth of clinically useful amount of tissues, since increasing the sizes of these types of bioreactors results in detrimentally large shear forces. An example of known industrial scale bioreactors is the Air Lift Bioreactor, which is a low energy input, high-yield alternative to stirred tank bioreactors that manages to achieve good oxygen transfer with low fluid shear. A limitation of the Air Lift Bioreactor is the mixing of mass transfer and oxygen availability limiting cell growth, and not allowing cultivation for high cell density required for practical application.

Thus, the present invention overcomes these known limitations and improves the physical environment of a bioreactor using a computational fluid dynamics (CFD) model that would allow for scaling-up from research size to industrial size, improving efficiency and increasing cell density in a controlled flow environment. This study focuses on flow perfusion bioreactors that allow for the design including features such as variable ("tided") flow, control of the flow through regions of least resistance and maintaining the flow through the scaffold.

To verify the viability of the various preferred embodiments of the present invention geometrical and mesh models were first simulated in three-dimensions by computer modeling. Bioreactor models were sketched using Pro/Engineering 2000i (PTC, Needham, Mass., USA). With Pro/Engineering, sketching in three dimensions was useful for progressive design modifications, and the sketches were compatible with the mesh used for flow simulations. The three designs considered in this study included a standard reactor with a double-bell-shape vessel (design 1, see FIG. 1), a pipe with a cylindrical vessel (design 2, see FIG. 4), and a standard reactor with internal irises (design 3, see FIGS. 7A and 7B).

Figure 7A:
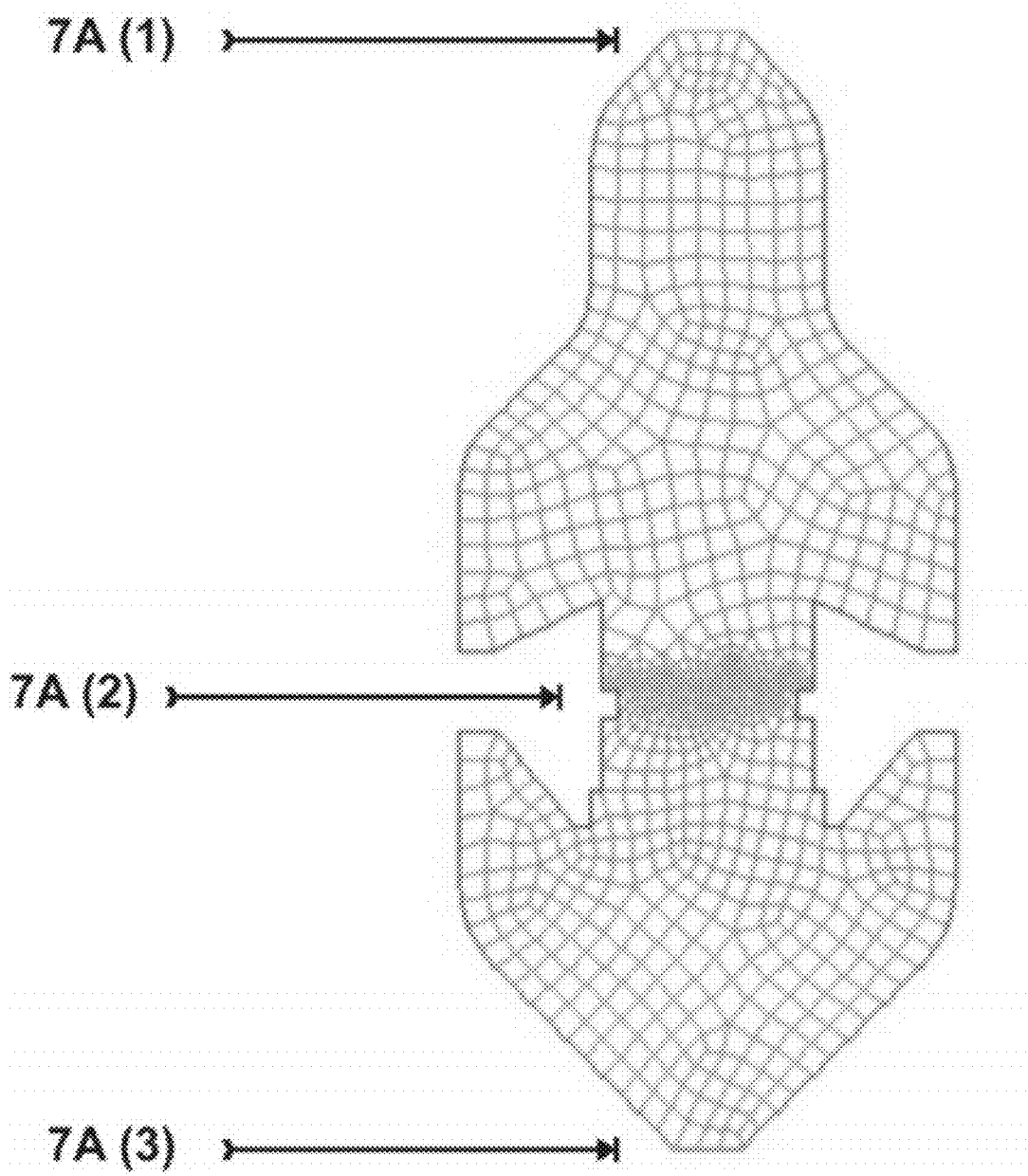
FIG. 7A is a representational front view of a third bioreactor according to a third embodiment of the present invention.
Figure 7B:
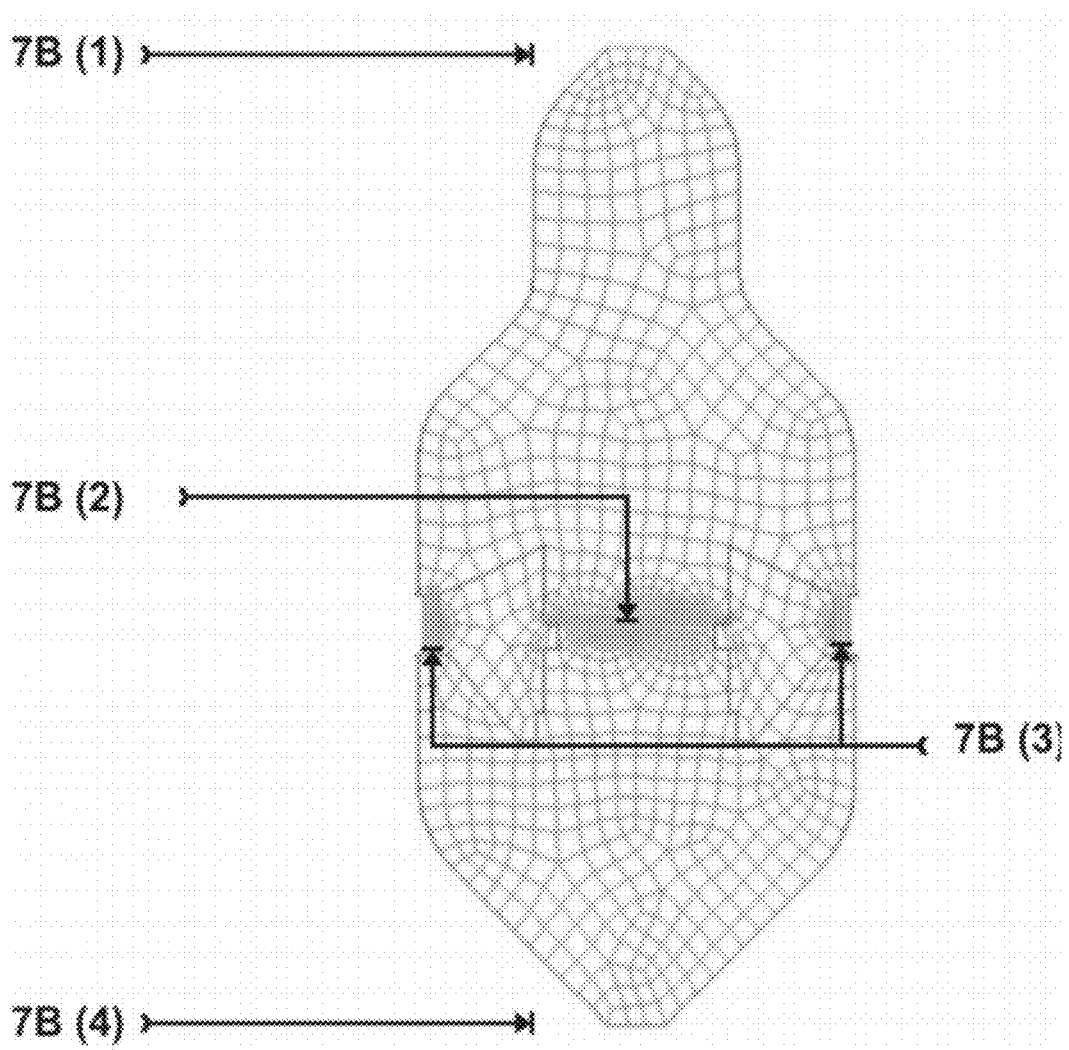
FIG. 7B is a representational front view of the third bioreactor of FIG. 7A but also includes an iris and bypass according to a preferred embodiment of the present invention.

The mesh of the bioreactor model was prepared using GAMBIT (ANSYS, Inc., Canonsburg, Pa., USA). A cross-section of the model was composed of 35000 (design 1), 65000 (design 2) and 80000 tetrahedral elements (design 3), respectively. For design 3, the porous region as well as the irises required a smaller mesh of 1.27×10−3 m when the flow path becomes very narrow (FIGS. 7A and 7B). The larger areas of fluid flow were meshed by 5.98×10−3 m. After transfer of the mesh into the CFD modeling software (FLUENT software, ANSYS, Inc. Canonsburg, Pa., USA), the grid was checked and scaled in inches.

The scaffold was simulated with a uniform porous medium model. The scaffold porosity was set within the range of 70-90% since the porosity for bone tissue is approximately 78%. In order to mimic various stages of cell proliferation within the porous scaffold, five different permeability values representing different stages of cell growth were chosen according to the literature. Scaffold thickness was set at 1 cm prior to scaling. Parameters for modeling of flow through porous media are summarized in Table 1 as FIG. 15 shows.

CFD modeling was performed using FLUENT software (ANSYS, Inc. Canonsburg, Pa., USA). A CFD simulation with the following parameters and boundary conditions was performed: Axisymmetric model, segregated solver, laminar fluid flow, incompressible Newtonian fluid with the viscosity of water at 37° C., no-slip boundary conditions on walls, atmospheric operating pressure and reference pressure location [0,0]. The inlet of the bioreactor was set in terms of either mass flow rate or velocity. For calculation of mass flow rate in kg s−1, the components of flow directions were set as [0, −1]. For flow velocity simulations, the inlet velocity was set at 7.34×10−5 m s−1 [33]. The convergence criterion was set at 0.001 for continuity, x-velocity and y-velocity. The number of iterations was set at 500 and if there was no convergence, factors for pressure and momentum were adjusted until the solution converged. Plots of flow velocity, pressure, velocity vectors and flow path lines were generated for the fluid analysis.

Laminar flow is determined by the Reynolds number. When fluid moves smoothly in parallel layers and the Reynolds number is lower than the critical value of 2000, the flow is assumed to be laminar, whereas for Reynolds numbers above 3000, the flow is considered to be turbulent [34]. The Reynolds number is calculated as:

$$RE = V*d/V;  \quad (1)$$

where V is the average flow velocity, d is the diameter of the bioreactor and v is the kinematic viscosity of water with v=10−6 m2 s−1=1 cSt at 20° C. [35]. The average flow velocity V is obtained from:

$$Q = V \times A;  \quad (2)$$

where Q is the volumetric flow rate and A is the cross-sectional flow area with:

$$A = (\text{pi} \times d^2)/4.  \quad (3)$$

For laminar flow of viscous fluids, the velocity increases towards the center of the scaffold and is a function of the radial location. The velocity is also inversely proportional to the viscosity of the fluid. The viscosity and permeability for the simulation are related by Darcy's Law:

$$Q/A = (k/u) \times (\text{delta } P/L);  \quad (4)$$

where k is the hydrodynamic permeability, u is the dynamic viscosity (considered to be the same as water at 20° C. with 0.001 Pa s), delta P is the pressure drop across the porous scaffold, and L is the thickness of the scaffold.

The Ergun equation below can be applied to calculate the pressure drop across a porous medium (packed bed model) by linearly combining the Blake-Kozeny model for laminar flow with the Burke-Plummer model for turbulent flow (the first and second terms on the right side of eqn. 5, respectively):

$$\text{Delta } P/L = (150u(1-E)^2 V)/(D_p^2 E^3) + 1.75 \times ((1-E)\rho V^2)/(E^3 D_p))  \quad (5)$$

where E is the porosity of the scaffold, ρ is the density of the fluid and Dp is the mean particle diameter of the porous medium. Related to this equation, the viscous resistance coefficient 1/k (which dominates at low Re) and the inertial resistance coefficient C2 (which dominates at high Re) can be derived as follows:

$$1/k = (150(1-E)^2/(D_p^2 \times E^3));  \quad (6)$$

$$C_2 = (3.5(1-E)/(D_p \times E^3)).  \quad (7)$$

Prototype testing and cell culture conditions.

Human adipose mesenchymal stem cells were derived from fat tissue of donors undergoing abdominoplasty after obtaining informed consent. Briefly, cells were isolated by collagenase digestion and sequential centrifugation according to standard protocols. Adipose mesenchymal stem cells were expanded in standard culture medium (DMEM-F12 (PAA laboratories, US), 5% FCS, supplemented with antibiotics, sodium pyuvate and non-essential amino-acids (all Biochrom, US)) and then seeded onto macroporous ceramic scaffolds (Sponceram® Zellwerk GmbH, Germany). Scaffolds were cultured under static conditions in a petridish inside a cell culture incubator at 37° C., 5% CO2, and under dynamic condition within the bioreactor prototype with continuous perfusion of 1 ml/min via a peristaltic pump (Ismatec, Germany) at 37° C. for 1 month in standard culture medium with HEPES buffer solution at 0.01 M (PAA Laboratories, US). Scaffold were stained with fluorescein diacetate 2.4 µmolL-1 (Sigma, Germany), washed with phosphate buffer saline (PAA laboratories, US) and cell vitality was analysed via stereomicroscopy (Olympus SZX16 Germany).

Results

Design 1:

The primary design (design 1, a first preferred embodiment of the present invention) was based on a standard perfusion bioreactor. The mesh model by GAMBIT is presented in FIG. 1. Flow simulations by FLUENT revealed significant problems with flow stagnation as well as relevant pressure build-up upstream of the reactor as demonstrated in FIGS. 2A and B. There was a significant decrease in flow velocity across the scaffold, which might adversely affect mass transport and oxygen transfer to the cells in the scaffold.

Figure 2A:
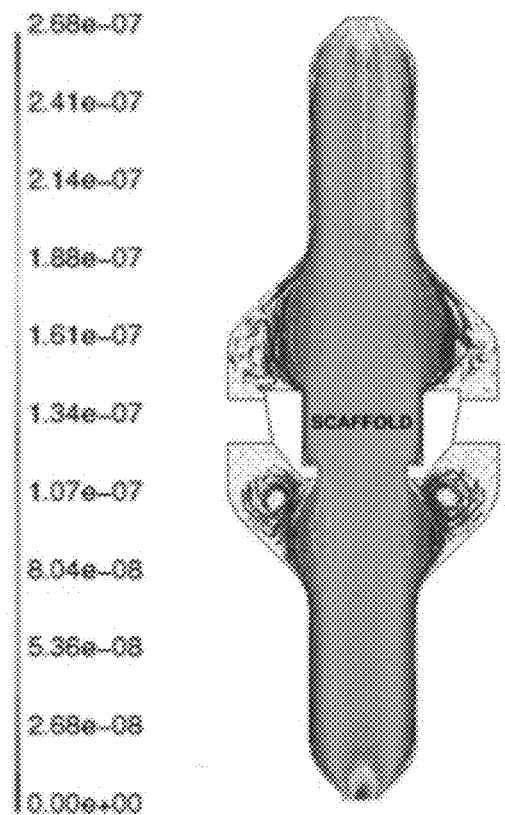
FIG. 2A is a diagram illustrating laminar flow path lines of a bioreactor according to one embodiment of the present invention.
Figure 2B:
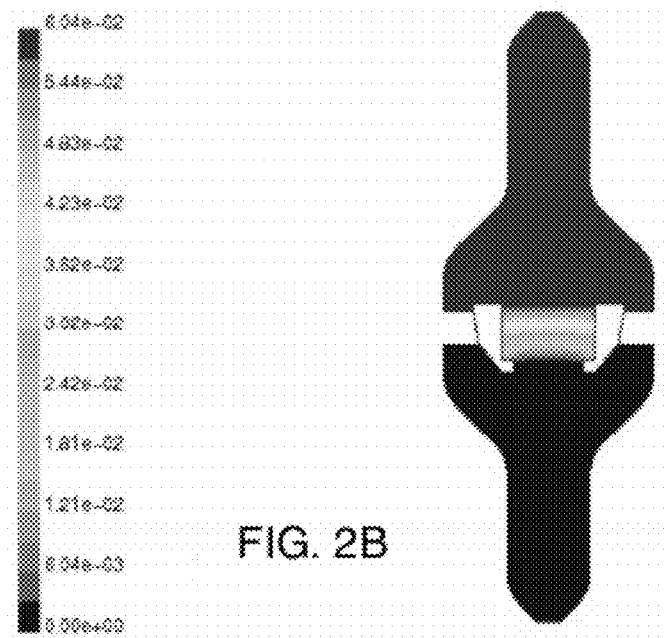
FIG. 2B is representational diagram illustrating pressure distribution in a bioreactor according to one embodiment of the present invention.

FIG. 2A illustrates flow path lines of bioreactor design 1 and highlights significant stagnation above and below scaffold level (velocity values in m s−1; e−08=×10−8). FIG. 2B shows a pressure distribution of bioreactor design 1 and reveals significant pressure build-up upstream of scaffold (pressure values in Pa; e−02=×10−2).

Figure 3:
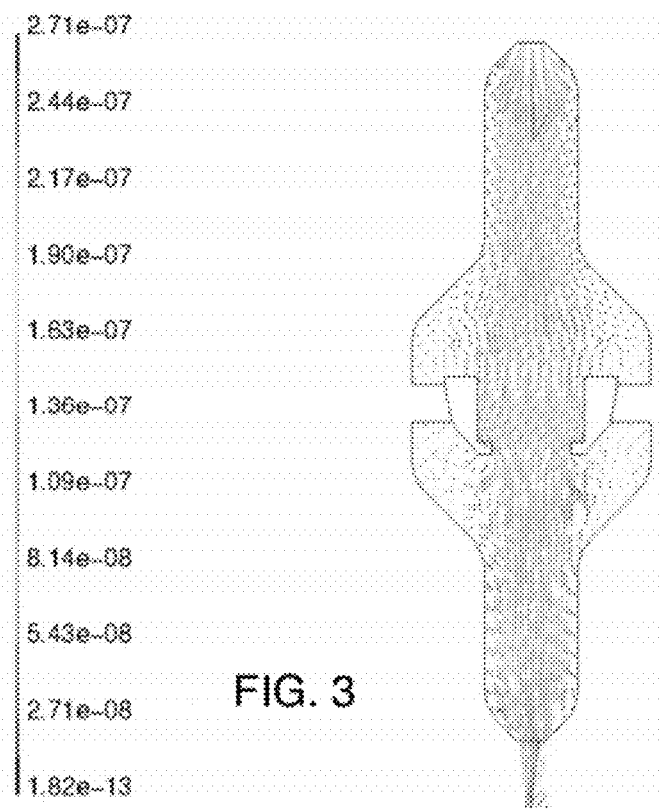
FIG. 3 is a representational diagram illustrating flow vectors according to a first contemplated embodiment of the present invention.

FIG. 3 shows the distribution of flow vectors that are not parallel (laminar) downstream of the scaffold. These results suggest that this design of the bioreactor needs to be improved in order to reduce flow stagnation and irregularities. These irregular currents downstream of scaffold, suggesting turbulence (velocity values in m s−1; e−08=×10−8).

Figure 4:
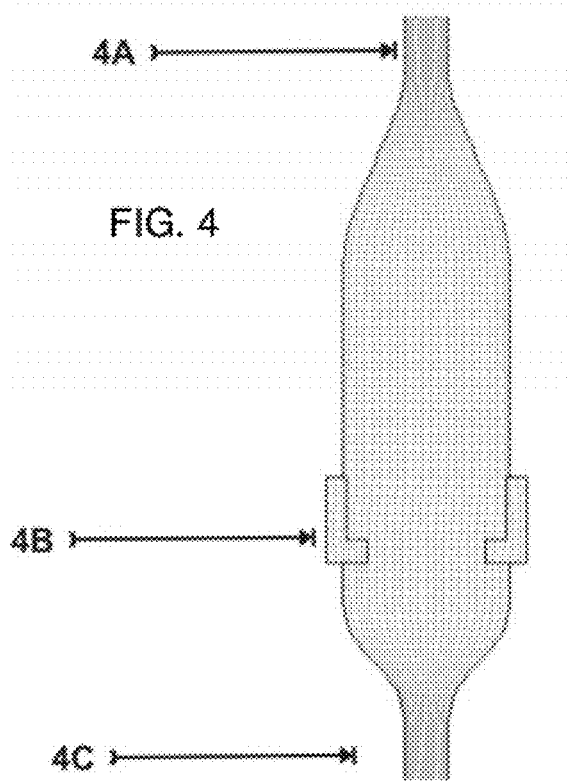
FIG. 4 is a representational front view of a second bioreactor according to a second embodiment of the present invention.

Design 2:

A second preferred embodiment of the present invention is based on the CFD results of design 1 whereby the geometry of the bioreactor was modified to resemble a pipe in order to optimize flow patterns. FIG. 4 shows the GAMBIT mesh of bioreactor design 2.

Figure 5A:
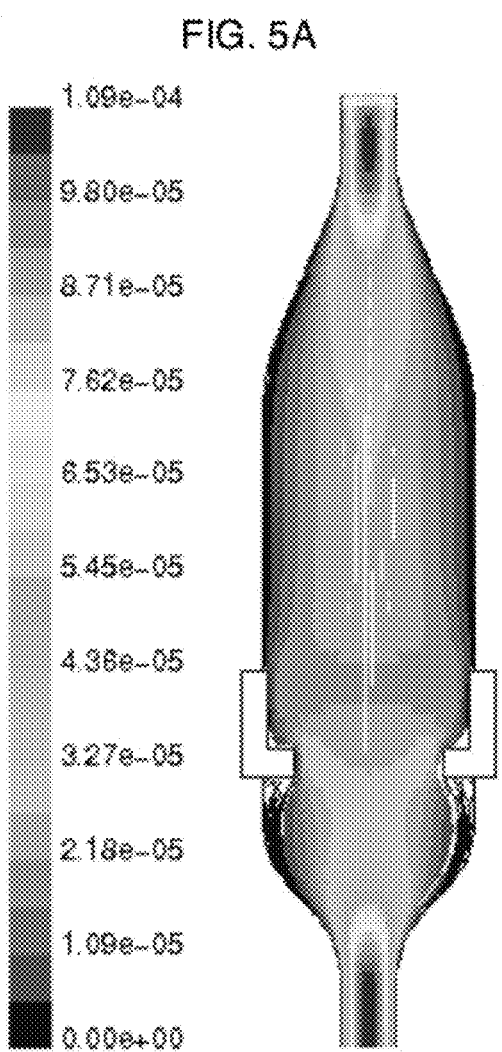
FIG. 5A is a diagram illustrating laminar flow path lines of the second bioreactor according to a second embodiment of the present invention.
Figure 5B:
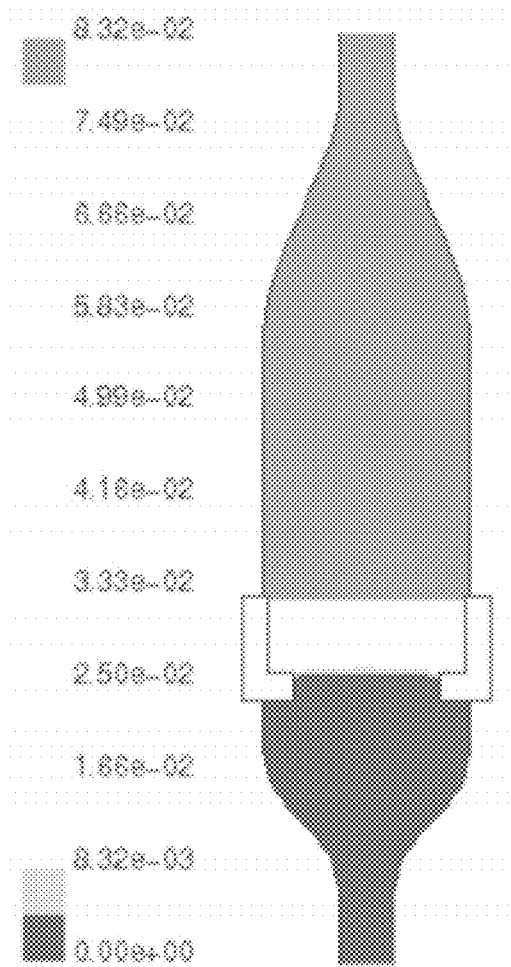
FIG. 5B is a representational diagram illustrating pressure distribution in a bioreactor according to a second embodiment of the present invention.
Figure 6:
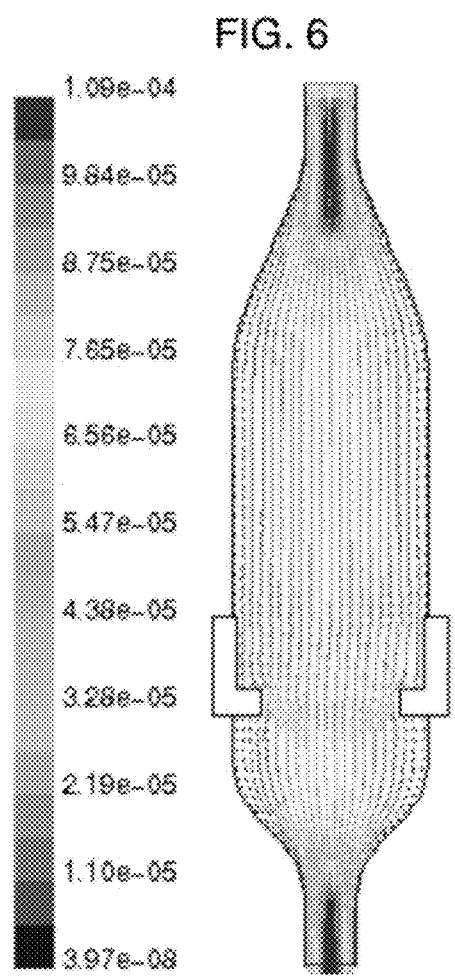
FIG. 6 is a representational diagram illustrating flow vectors according to a second embodiment of the present invention.

Results of flow simulation by FLUENT software are presented in FIGS. 5 and 6, demonstrating flow path lines more regular with less stagnation compared to design 1 (velocity values in m s−1; e−05=×10−5) (FIG. 5A) but there was still a significant pressure build-up in the upper half of the vessel (FIG. 5B). FIG. 5B shoes a pressure distribution of bioreactor design 2 (pressure values in Pa; e−02=×10−2). And, flow vectors are more regular and parallel to each other, suggesting laminar flow pattern, than in design 1, as shown in FIG. 6 (velocity values in m s−1; e−05=×10−5).

Design 3:

A third preferred embodiment of the present invention improved undesirable performance criterion of both of the previous designs. From the simulation results of those designs, we learned that a bypass system would be conducive to releasing pressure build-up in the system and preventing flow irregularities. Therefore, irises were introduced to our design 3 in order to control the flow and pressure in the bioreactor. The iris system opens and closes like the iris of eye, and can be controlled by pressure sensors installed upstream and downstream of the scaffold in the bioreactor. Although the openings of these irises were adjustable, they were set as completely closed or completely open in our simulation. FIG. 7 demonstrates the mesh for design 3 using GAMBIT solid geometry Modeler and GAMBIT mesh modeler given the flow domain. FIG. 7A shows the design with closed irises, where the main low field was meshed with a mesh size of 5.98×10 3 m.

FIG. 7A shows one possible mesh for bioreactor design 3 with a mesh size of 5.98×10−3 m for the main flow field and finer mesh size of 1.27×10−3 m at the scaffold level.

In order to model the design with open irises as shown in FIG. 7B, a finer mesh size of 1.27×10 3 m was adopted since the open flow path became very narrow.

Figure 9:
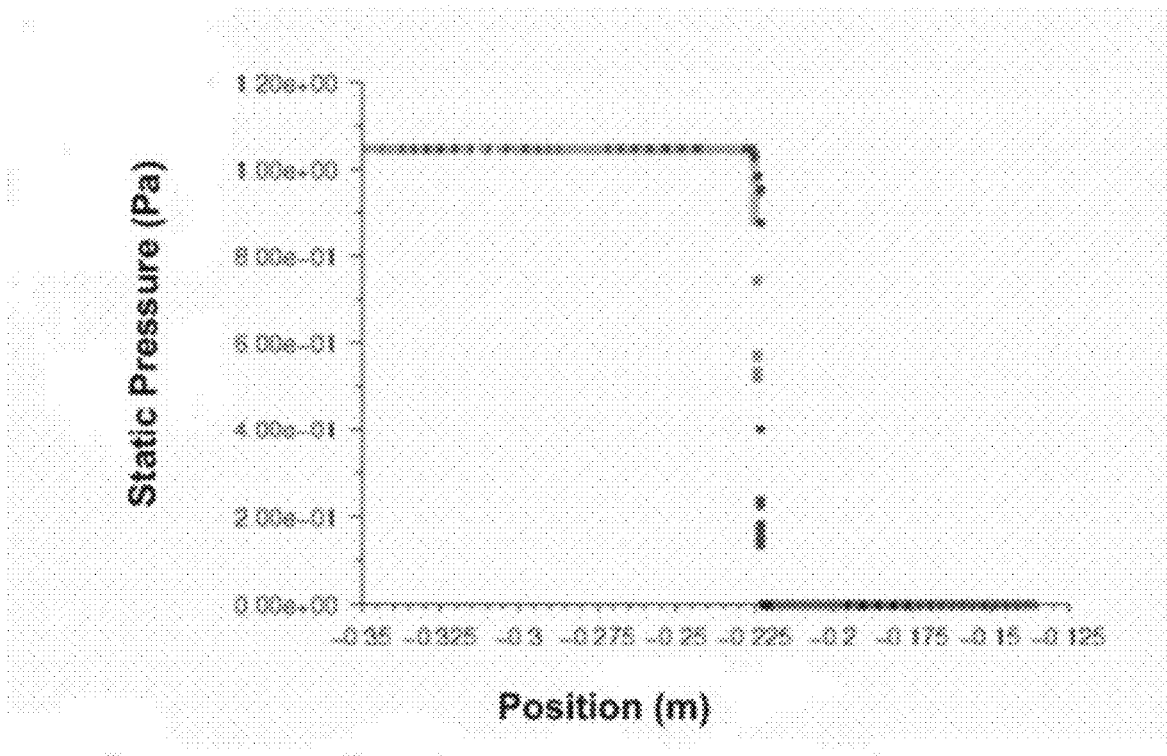
FIG. 9 is a graph showing the pressure variation across the scaffold in the third bioreactor according to one embodiment of the present invention.
Figure 10:
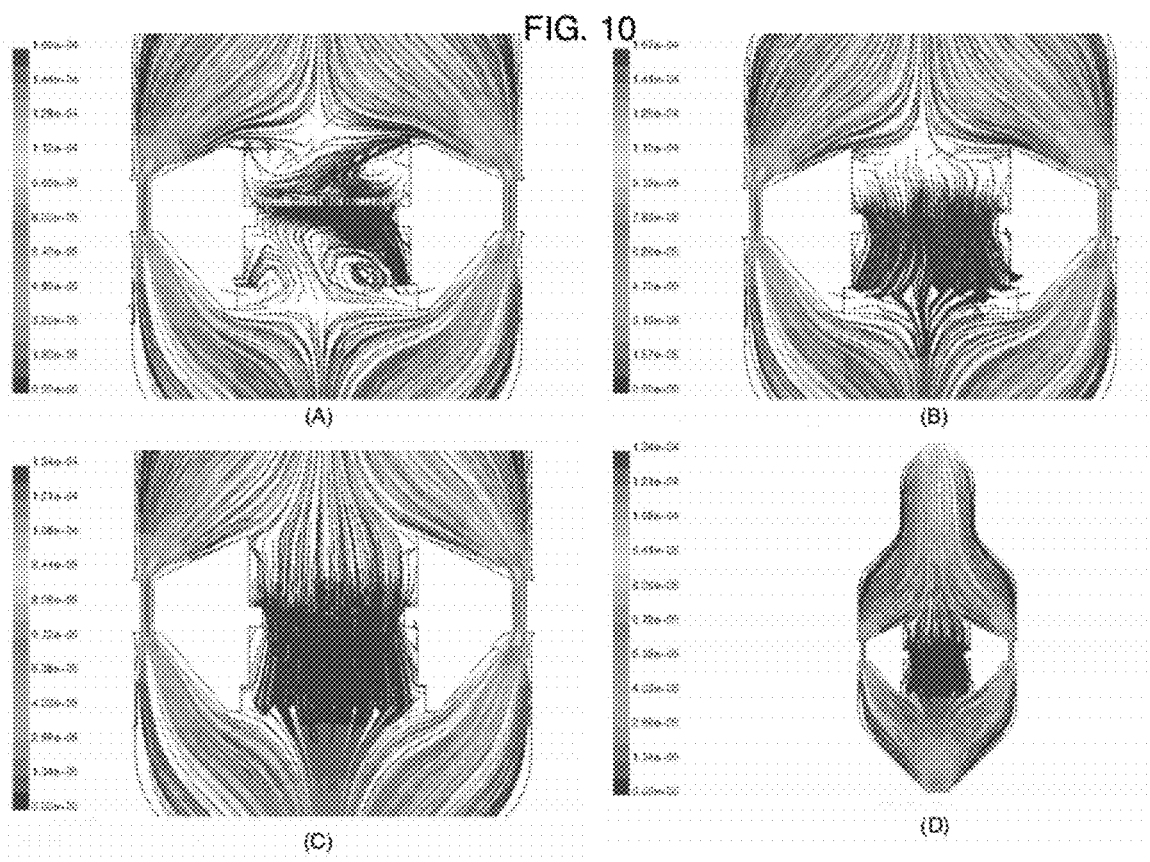
FIG. 10 is a representational diagram illustrating laminar flow path lines of the third bioreactor according to one embodiment of the present invention.
Figure 11:
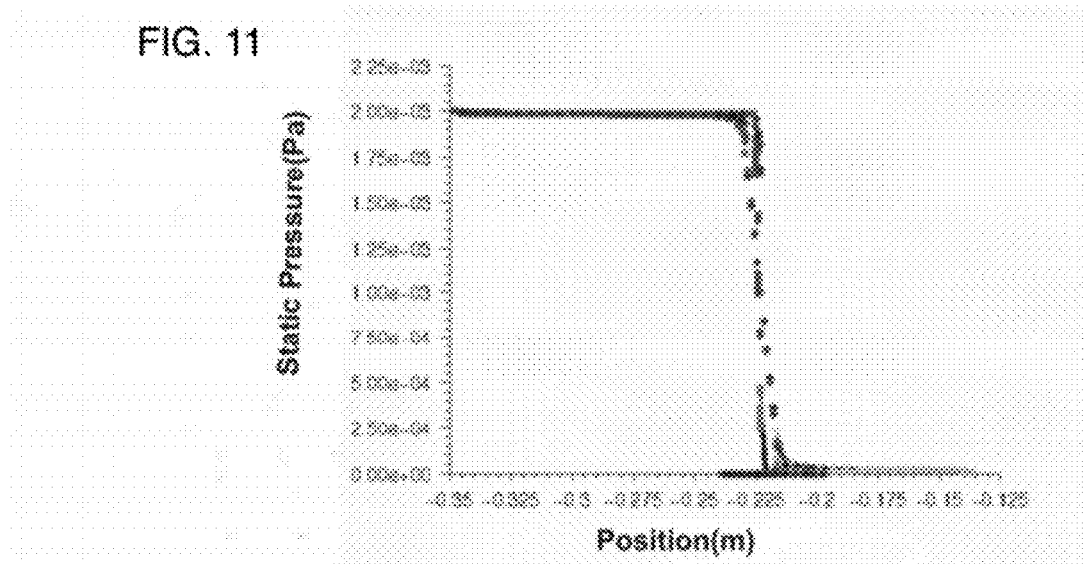
FIG. 11 is a graph showing the pressure variation across the scaffold with the iris in the open position in the third bioreactor according to one embodiment of the present invention.

CFD simulations of design 3 exemplary for some scaffold permeability values (Table 1, illustrated by FIG. 15) are exhibited in FIG. 8 (flow path lines) and FIG. 9 (pressure drop across scaffold) for closed irises, as well as in FIG. 10 (flow path lines) and FIG. 11 (pressure drop across scaffold) for open irises.

FIG. 8 shows flow path lines of bioreactor design 3 with closed irises showing some stagnation at scaffold level, exemplary shown for permeability=5×10−9 m2 in partial (A) and full view (B) (velocity in m s−1; e−05=×10−5).

FIG. 9 illustrates pressure variation across the scaffold in bioreactor design 3 showing pressure drop of 1.05 Pa at the scaffold for permeability 5×10−9 m2, (inlet position −0.35 m, scaffold position −0.225 m, outlet position −0.125 m).

In this third preferred embodiment when irises were closed, fluid flow did not converge for the lowest permeability 4.5×10−13 m2 and 5×10−12 m2, and even with open irises, there were some flow irregularities for these values of permeability (FIG. 10 A). However, at higher values of permeability, there was laminar flow at scaffold level when irises were open (FIG. 10 B-D).

FIG. 10 illustrates flow path lines of bioreactor design 3 with open irises. This shows some flow perturbation at low values of permeability, exemplary shown for permeability=5×10−12 m2 (A), but laminar flow at higher values of permeability (permeability=5×10−10 m2 (B) and 5×10−9 m2 (C)). FIG. 10F shows a full view for permeability=5×10−9 m2 (Velocity in m s−1; e−05=×10−5). A comparison of CFD simulation results for pressure variation across the scaffold in different three preferred embodiment (designs 1,2 and 3) of bioreactor of the present invention are presented in Table 2, which is represented in FIG. 16. From this it is clear that the bypass mechanism, specifically when operated in the "open" position by opening iris system significantly reduced the pressure drop across the scaffold from 1.05 Pa to 2.0×10−3 Pa (FIGS. 9 and 11, simulated for permeability of 5×10−9 m2).

FIG. 11 shows pressure variation across the scaffold in bioreactor design 3 with open irises with a significantly reduced pressure drop of 2×10−3 Pa at the scaffold for permeability of 5×10−9 m2, (inlet position −0.35 m, scaffold position −0.225 m, outlet position −0.125 m).

Figure 12:
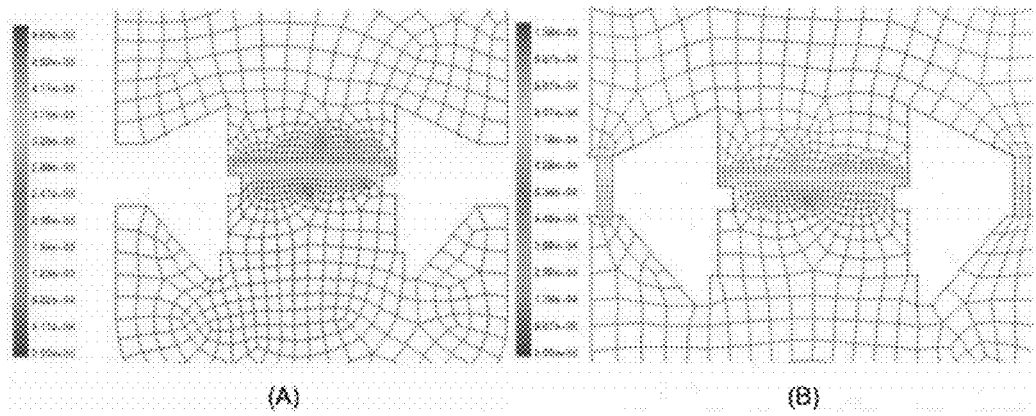
FIG. 12 is a representational diagram illustrating the difference of pressure distribution with the scaffold closed or open in the third bioreactor according to a third embodiment of the present invention.

FIG. 12 presents a closer view of pressure distribution at scaffold level for closed (FIG. 12A) and open irises (FIG. 12B). The calculated Reynolds number with closed irises was 2942, indicating turbulence with high pressure drop and shear, while opening of the iris reduced the Reynolds number to 641, indicating laminar flow. Table 2 summarizes results of CFD simulation for pressure distribution of the three designs, where opening of the iris system in design 3 allows decrease of high pressure upstream of the scaffold.

FIG. 12 illustrates the pressure distribution of bioreactor design 3 around the scaffold with closed (A) and open (B) irises. (Pressure in Pa; e−04=×10−4).

Figure 13:
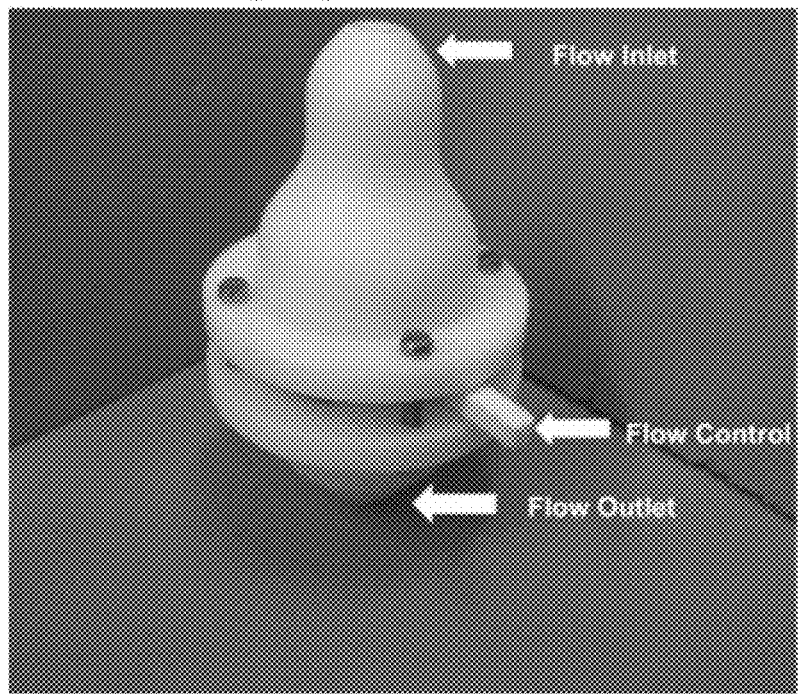
FIG. 13 is a photograph showing the front view of the third bioreactor according to one embodiment of the present invention.

Based on results of the CFD modeling, a prototype reactor was built as shown in FIG. 13. Results of biological experiments with human adipose mesenchymal stem cells cultured in a macroporous ceramic scaffold demonstrated constant high cellular viability after 1 month of dynamic culture within the bioreactors, as shown in FIG. 14A, in contrast to static culture in the petridish (FIG. 14B).

Figure 14:
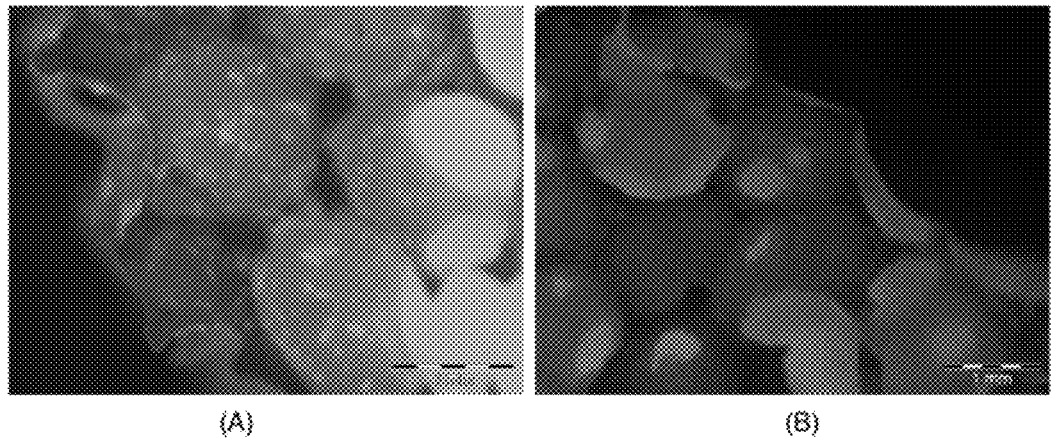
FIG. 14 is a photograph showing the dynamic cultivation of cell-seeded scaffolds in the third bioreactor according to one embodiment of the present invention.

FIG. 14 illustrates the dynamic cultivation of cell-seeded scaffolds in the prototype bioreactor promotes cell vitality in contrast with static culture. Adipose mesenchymal stem cells are cultivated on a macorporous ceramic scaffold (section) for 1 month under continuous perfusion in the bioreactor (A) versus static culture in a petridish (B). Cells were stained with fluorescein diacetate and observed under an Olympus stereomicroscope.

Discussion

Different perfusion bioreactors have been developed for tissue engineering applications, especially for bone tissue engineering. However, many systems were characterized only by perfusion rate and lack substantial information about shear stress within the reactor vessel. The results of our study suggest that reactor geometry has a significant impact on flow perfusion and pressure distribution around the scaffold. Common designs such as bell-shaped and cylindrical vessels cannot guarantee continuous perfusion across scaffolds without creating areas of flow stagnation or pressure build-up, as demonstrated in our CFD simulation results. Furthermore, our results show that increase in permeability of the scaffold due to cellular growth has an impact on flow vectors and pressure distribution.

In our approach, we focused on modeling of flow path lines within a reactor vessel and across the scaffold with different values of permeability due to cellular growth. However, we did not study the shear stress within the scaffold itself. For this issue, the interconnectivity and tortuosity of scaffold pores as well as cellular growth within the pores need to be considered. Calculations will require precisely defined scaffold geometry through, e.g., CT scanning, and infinite elements analysis tools. Recent studies on CFD modeling have been performed on modeling fluid flow through regular and irregular scaffolds during perfusion without considering reactor shape.

From the analysis of the different designs, it was apparent that optimizing the geometry of the reactor was necessary to reduce flow irregularities. Designs 2 and 3 did not have as much flow stagnation as design 1, even when the irises in design 3 were closed. The pressure build-up in design 2 was undesirable despite its regular flow pattern with little stagnation.

FIG. 17 shows an improved laminar flow bioreactor 10 for three-dimensional cell growth. The bioreactor 10 includes reactor vessel 12 defining a chamber 14 comprising an upper house 16 and a lower house 18, the upper house having an inlet aperture 20 and the lower house having an outlet aperture 22, and the first and lower house s adapted to couple together.

The bioreactor 10 further includes a scaffold-insertion area 24 defined in the chamber at a position intermediate to the inlet aperture and outlet apertures. The bioreactor further includes an iris assembly 26 in selective fluid communication with the chamber 14 and adapted to create a bypass mechanism 28 by flow passages 29 and 30 around the scaffold-insertion area to allow fluid to flow from the upper house 16 to the lower house 18 (the direction of flow of the system from the inlet 20 to the outlet 22.

The iris assembly 26 includes at least one slot 32 (not visible in FIG. 17) and preferably a plurality of slots consisting of at least four slots, arranged on the iris 26 to align with the bypass mechanism comprising 28 in the open position and partially aligned with the bypass mechanism in at least one intermediate position, and to block flow between the upper and lower houses when in the closed position. To assist with manual operation of the iris, the iris assembly 26 includes a handle 34, which extends outside the chamber. Accordingly, the handle is adapted to operate from one position to a second position whereby the handle is adapted variably operate from a fully open to a fully close an at least one fluid communication passage from the upper house to the lower house whereby at least one fluid communication passage bypasses the scaffold-insertion area 35.

Figure 19:
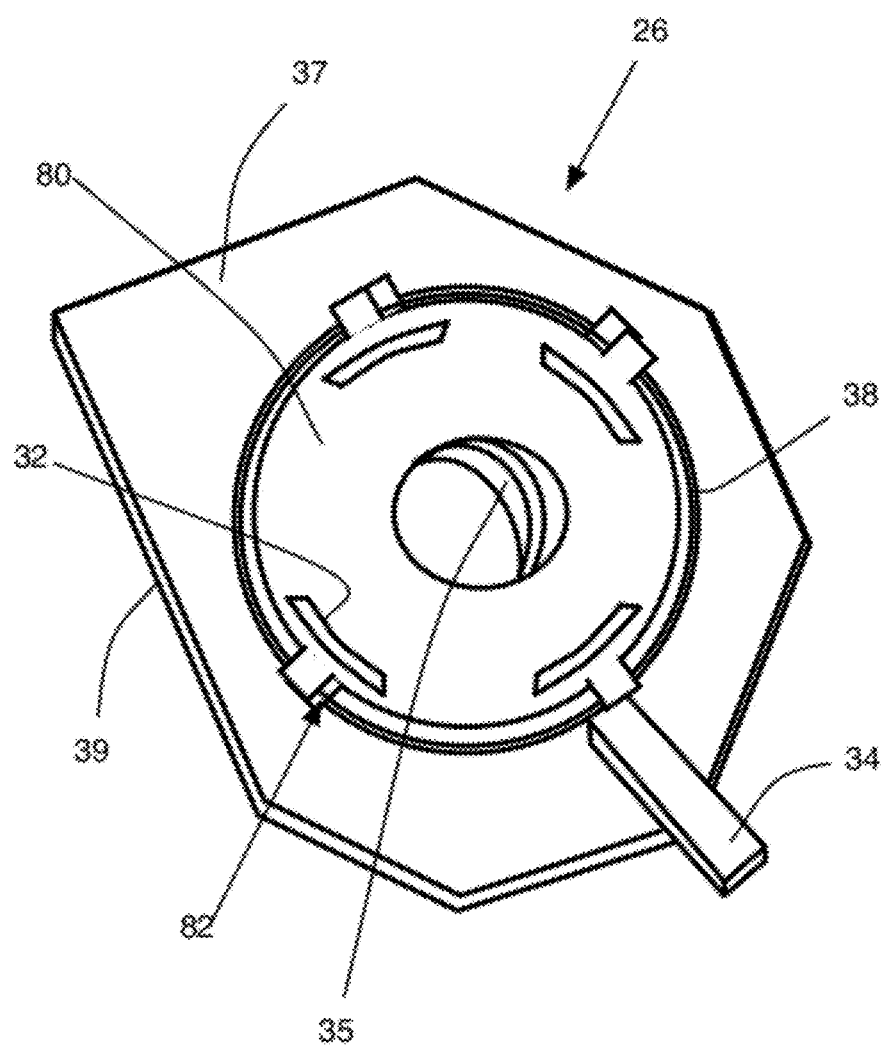
FIG. 19 is an offset top view of the iris relative to the scaffold in a partial cross section of a bioreactor according to one embodiment of the present invention.

The iris assembly 26 and/or at least one house includes means to provide support for a scaffold basket 36, such means include an iris clamp 38. To improve sealing, the iris assembly includes a first ring 80 and second ring 82 disposed on either side of the iris clamp 38. Some of these features, above, are better depicted in FIGS. 19-21.

The iris assembly 26 is disposed intermediate to the upper house and the lower house; and the iris clamp comprising a generally flat disk comprising a top face and an opposite bottom face and at least one slot-like aperture extending from the top face to the bottom face, and a handle-portion extending from the top face.

The upper house further comprising a first-housing flange 37 disposed adjacent to a first-housing proximal end, the first-housing proximal end being disposed opposite the inlet aperture and the lower house further comprising a second-housing flange 39 disposed adjacent to a second-housing proximal end, the second-housing proximal end being disposed opposite the outlet aperture.

Figure 20:
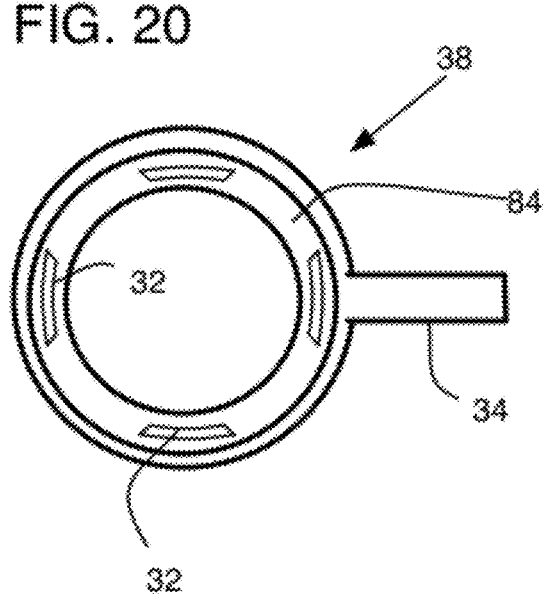
FIG. 20 is a top view of one preferred embodiment of an iris used in the various embodiments of a bioreactor according to the present invention. according to one embodiment of the present invention.

As better appreciated in FIG. 20, the iris clamp 38 consists generally of a flat disk having a top face 84 and an opposite bottom face and at least one slot-like aperture 32 extending from the top face to the bottom face, and a handle-portion 34 extending from the top face whereby a portion of the handle extends beyond an outside wall of the chamber.

Figure 18:
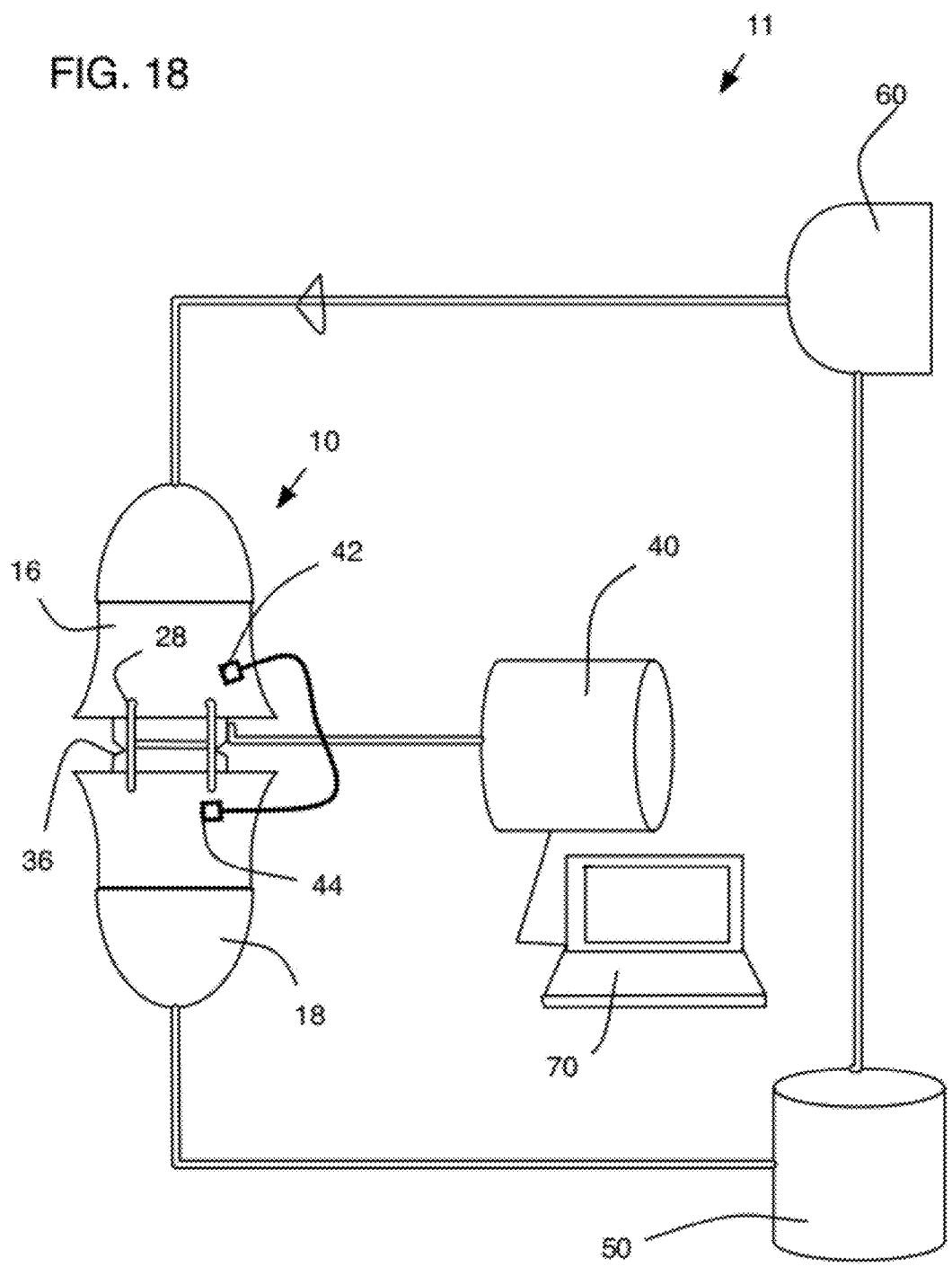
FIG. 18 is a schematic diagram of a system incorporating a bioreactor according to one embodiment of the present invention.
Figure 21:
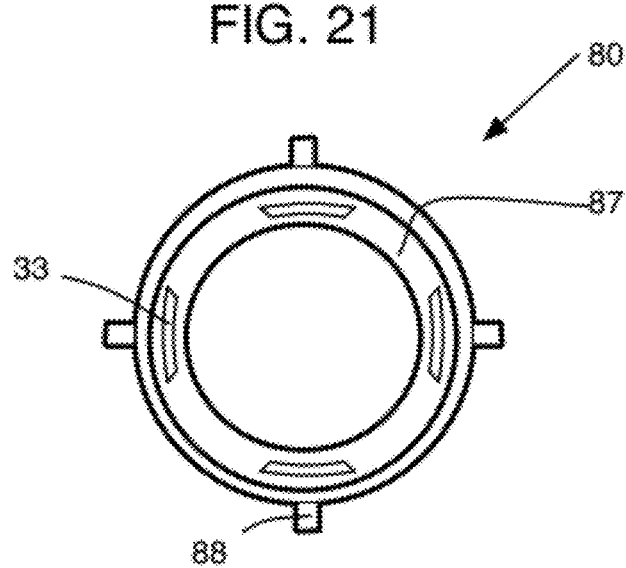
FIG. 21 is a top view of one preferred embodiment of a ring used in the various embodiments of a bioreactor according to the present invention.

FIG. 21 illustrates both the first and second rings 80 and 82 used in the system of FIG. 18 and the bioreactor of FIG. 17. Because both rings are essentially the same in configuration and material (stainless-steel) only one ring 80 is described herein. The ring 80 has a top face 87 and bottom face and at least one, and preferably four slots 33 arranged on the top face to provide a fluid path from one side of the ring to the other. The ring 80 includes at least one notch-feature 88 to help locate the ring and to prevent rotation of the ring when placed between the upper and lower houses of the bioreactor. Thus, when the iris 38 is rotated relative to the ring, the slots 33 align relative to the slots 32 of the iris and the bypass mechanism operates from an open to a closed position.

FIG. 18 shows a system 11 of the present invention using any of the preferred bioreactors discussed, above, but preferably, the bioreactor 10 illustrated in FIG. 17. As such, the bioreactor 10 has a chamber 14 defined by the upper house 16 cooperating with the lower house 18. A scaffold basket 36 inserts between the two houses and allows fluid to flow over a cell-sample to promote cell growth in the system 11. A bypass mechanism 28 is selectively controllable to allow some of the fluid to flow around, or bypass, the scaffold basket 36 by being operable from a closed position (no flow in the bypass, all flow is in the scaffold region) to a fully open position (bypass flows some fluid, in combination with flow in the scaffold region), or to an intermediate position.

This laminar flow bioreactor system 11, in addition to the bioreactor of FIG. 17, further includes a control box 40 comprising a first pressure sensor 42 arranged in the chamber at a location in the upper house and a second pressure sensor 44 arranged in the chamber at a location in the lower house.

This system 11 further includes a culture reservoir 50 in fluid communication with the bioreactor 10, and a pump 60 in fluid communication with the bioreactor and culture reservoir and all necessary conduits, valves, control mechanism, and monitoring equipment including hardware and software and programming and a computer 70, as would be understood by those skilled in the art.

Making general reference to FIGS. 17-21, the system 11 of FIG. 18 further contemplates that the iris clamp consists of a generally flat disk having a top face 84 and an opposite bottom face and at least one slot-like aperture extending from the top face to the bottom face, and a handle-portion 34 extending from the top face. To facilitate sealing the upper and lower chamber portions of the bioreactor, the upper house further comprising a first-housing flange 37 disposed adjacent to a first-housing proximal end, the first-housing proximal end being disposed opposite the inlet aperture. And, the lower house 18 further includes a second-housing flange 39 disposed adjacent to a second-housing proximal end, the second-housing proximal end being disposed opposite the outlet aperture.

Although the invention has been particularly shown and described with reference to certain embodiments, it will be understood by those skilled in the art that various changes in form and detail may be made without departing from the spirit and scope of the invention.

We claim:

1. An improved laminar flow bioreactor for three-dimensional cell growth, the bioreactor comprising:
   a reactor vessel defining a chamber comprising an upper house and a lower house, the upper house having an inlet aperture and the lower house having an outlet aperture, the first and lower houses adapted to couple together;
   a scaffold-insertion area defined in the chamber at a position intermediate to the inlet aperture and outlet aperture;
   an iris assembly configured to surround at least a portion of the scaffold-insertion area, the iris assembly comprising at least one slot arraned to align with a bypass mechanism wherein each of at least one slot is commonly operable from an open position to a closed position and at least one intermediate position, the iris assembly further being in variable selective fluid communication with the chamber; the bypass mechanism comprising at least one flow passage extending from the upper house to the lower house and further disposed outside the scaffold-insertion area, the iris assembly further comprising a handle extending outside the chamber, whereby the handle is adapted to operate from one position to a second position whereby the handle is adapted variably operate from a fully open to a fully close the at least one slot relative to the at least one flow passage thus enabling an alternate flow passage from the upper house to the lower house that bypasses the scaffold-insertion area;

at first pressure sensor disposed between the scaffold-insertion area and the inlet aperture arranged in the chamber at a location in the upper house; a second pressure sensor disposed between the scaffold-insertion area and the outlet aperture arranged in the chamber at a location in the lower house; and wherein the bypass mechanism further comprises at least a first flow passage and a second flow passage arranged around the scaffold-insertion area and configured to allow fluid to flow from the upper house to the lower house independent from the scaffold-insertion area whereby fluid is enabled to bypass the iris assembly and travel to and from the upper house and the lower house.

2. The iris assembly of claim 1 further comprising:
an iris clamp adapted to provide support for a scaffold basket.

3. The iris assembly of claim 2 further comprising:
the iris assembly disposed intermediate to the upper house and the lower house; and
wherein the plurality of apertures comprises the iris clamp comprising a generally flat disk comprising a top face and an opposite bottom face and at least one slot-like aperture corresponding to each of the plurality of aperatures, and each slot-like aperture extending from the top face to the bottom face, and a handle-portion extending from the top face.

4. The bioreactor of claim 1 further comprising:
the upper house further comprising a first-housing flange disposed adjacent to a first-housing proximal end, the first-housing proximal end being disposed opposite the inlet aperture;
the lower house further comprising a second-housing flange disposed adjacent to a second-housing proximal end, the second-housing proximal end being disposed opposite the outlet aperture; and
the iris assembly further comprising an iris clamp comprising a generally flat disk comprising a top face and an opposite bottom face and at least one slot-like aperture extending from the top face to the bottom face, and a handle-portion extending from the top face whereby a portion of the handle extends beyond an outside wall of the chamber.

5. A bioreactor system comprising:
an improved laminar flow bioreactor comprising
a chamber defined by a upper house and a lower house cylinder, the upper house having an inlet aperture and the lower house having an outlet aperture, the first and lower house s adapted to couple together;
a scaffold-basket disposed between the upper house and the lower house; scaffold-insertion area defined in the chamber at a position intermediate to the inlet aperture and outlet aperture;
an iris assembly, the iris assembly comprising an iris clamp comprising a generally flat disk having a top face and an opposite bottom face and at least one slot-like aperture extending from the top face to the bottom face, and a handle-portion extending from the top face wherein the aperatures are commonly operable from an open position to a closed position and at least one intermediate position, the iris assembly further being in selective fluid communication with the chamber and adapted to create a bypass mechanism disposed around the scaffold-basket, the iris assembly comprising a handle extending outside the chamber, whereby the handle is adapted to operate from one position to a second position whereby the handle is adapted variably operate from a fully open to a fully closed position and at least one intermediate position the flat disk being rotatably mounted in the chamber in a plane perpendicular to a longitudinal axis extending from the upper house to the lower house whereby rotation of the flat disk positions the at least one slot-like aperture relative to the bypass mechanism to selectively create an alternate fluid communication path from the upper house to the lower house that bypasses the scaffold basket;
the iris assembly further comprising an iris clamp adapted to provide support for the scaffold basket;
a control box comprising
a first pressure sensor arranged in the chamber at a location in the upper house and a second pressure sensor arranged in the chamber at a location in the lower house cylinder;
a culture reservoir in fluid communication with the bioreactor; and a pump in fluid communication with the bioreactor and culture reservoir; and
wherein the bypass mechanism comprises at least a first flow passage and a second flow passage around the scaffold-insertion area and configured to allow fluid to flow from the upper house to the lower house whereby fluid is enabled to bypass the iris assembly and travel to and from the upper house and the lower house .

* * * * *